United States Patent
Ghayur et al.

(10) Patent No.: US 6,187,550 B1
(45) Date of Patent: Feb. 13, 2001

(54) METHODS AND CELL LINES FOR SCREENING COMPOSITIONS AND GENES FOR ABILITY TO INTERACT WITH IL-1β AND ICE PROCESSING

(75) Inventors: Tariq Ghayur, Grafton; Lorraine M. McGuinness, Peabody, both of MA (US)

(73) Assignee: BASF AG, Worchester, MA (US)

(*) Notice: Under 35 U.S.C. 154(b), the term of this patent shall be extended for 0 days.

(21) Appl. No.: 08/748,547

(22) Filed: Nov. 13, 1996

Related U.S. Application Data

(63) Continuation of application No. 08/280,889, filed on Jul. 27, 1994, now abandoned.

(51) Int. Cl.⁷ .................................................. G01N 33/573
(52) U.S. Cl. .................. 435/7.4; 435/7.8; 435/172.1; 435/69.1; 435/325; 435/358; 435/360; 435/364; 435/365; 435/365.1; 435/252.3; 435/320.1; 530/350; 536/23.5
(58) Field of Search .................. 435/7.4, 7.8, 172.1, 435/69.1, 325, 358, 360, 364, 365, 365.1, 252.3, 320.1; 530/350; 536/23.5

(56) References Cited

U.S. PATENT DOCUMENTS 5,416,013 * 5/1995 Black et al. .................. 435/226

OTHER PUBLICATIONS

F.M. Wurm, "Integration, Amplification and Stability of Plasmid Sequences in CHO Cell Cultures", Biologicals 18:159–164, 1990.*
N.A. Thornberry et al., Nature 356(6372):768–774, Apr. 30, 1992.*
P.A. Krasney et al., Cytokine 4(2):143–143, Mar. 1992.*
D.P. Cerretti et al., Science 256:97–100, Apr. 3, 1992.*
C. Baldari et al., EMBO J. 6(1):229–234, Jan. 1987.*

* cited by examiner

*Primary Examiner*—Lorraine Spector
(74) *Attorney, Agent, or Firm*—Lahive & Cockfield, LLP; Giulio A. DeConti, Jr.; Elizabeth A. Hanley

(57) ABSTRACT

Embodiments of the present invention are directed to non-naturally occurring cells and methods for screening compositions and genes which interact with interleukin 1 beta and interleukin-1 beta converting enzyme (ICE) processing, methods and non-naturally occurring cells for making ICE, and agonists and inhibitors of ICE.

39 Claims, 19 Drawing Sheets

Nucleic Acid Sequence for preICE and Corresponding
Amino Acid Sequence

| | | | | | | | | | | | | | | | | |
|---|---|---|---|---|---|---|---|---|---|---|---|---|---|---|---|---|
| ATG | GCC | GAC | AAG | GTC | CTG | AAG | GAG | AAG | AGA | AAG | CTG | TTT | ATC | CGT | TCC | 48 |
| Met | Ala | Asp | Lys | Val | Leu | Lys | Glu | Lys | Arg | Lys | Leu | Phe | Ile | Arg | Ser | |
| 1 | | | | 5 | | | | | 10 | | | | | 15 | | |
| ATG | GGT | GAA | GGT | ACA | ATA | AAT | GGC | TTA | CTG | GAT | GAA | TTA | TTA | CAG | ACA | 96 |
| Met | Gly | Glu | Gly | Thr | Ile | Asn | Gly | Leu | Leu | Asp | Glu | Leu | Leu | Gln | Thr | |
| | | | 20 | | | | | 25 | | | | | 30 | | | |
| AGG | GTG | CTG | AAC | AAG | GAA | GAG | ATG | GAG | AAA | GTA | AAA | CGT | GAA | AAT | GCT | 144 |
| Arg | Val | Leu | Asn | Lys | Glu | Glu | Met | Glu | Lys | Val | Lys | Arg | Glu | Asn | Ala | |
| | | 35 | | | | | 40 | | | | | 45 | | | | |
| ACA | GTT | ATG | GAT | AAG | ACC | CGA | GCT | TTG | ATT | GAC | TCC | GTT | ATT | CCG | AAA | 192 |
| Thr | Val | Met | Asp | Lys | Thr | Arg | Ala | Leu | Ile | Asp | Ser | Val | Ile | Pro | Lys | |
| | 50 | | | | | 55 | | | | | 60 | | | | | |
| GGG | GCA | CAG | GCA | TGC | CAA | ATT | TGC | ATC | ACA | TAC | ATT | TGT | GAA | GAA | GAC | 240 |
| Gly | Ala | Gln | Ala | Cys | Gln | Ile | Cys | Ile | Thr | Tyr | Ile | Cys | Glu | Glu | Asp | |
| 65 | | | | | 70 | | | | | 75 | | | | | 80 | |
| AGT | TAC | CTG | GCA | GGG | ACG | CTG | GGA | CTC | TCA | GCA | GAT | CAA | ACA | TCT | GGA | 288 |
| Ser | Tyr | Leu | Ala | Gly | Thr | Leu | Gly | Leu | Ser | Ala | Asp | Gln | Thr | Ser | Gly | |
| | | | | 85 | | | | | 90 | | | | | 95 | | |
| AAT | TAC | CTT | AAT | ATG | CAA | GAC | TCT | CAA | GGA | GTA | CTT | TCT | TCC | TTT | CCA | 336 |
| Asn | Tyr | Leu | Asn | Met | Gln | Asp | Ser | Gln | Gly | Val | Leu | Ser | Ser | Phe | Pro | |
| | | | | 100 | | | | | 105 | | | | | 110 | | |
| GCT | CCA | CAG | GCA | GTG | CAG | GAC | AAC | CCA | GCT | ATG | CCC | ACA | TCC | TCA | GGC | 384 |
| Ala | Pro | Gln | Ala | Val | Gln | Asp | Asn | Pro | Ala | Met | Pro | Thr | Ser | Ser | Gly | |
| | | 115 | | | | | 120 | | | | | 125 | | | | |
| TCA | GAA | GGG | AAT | GTC | AAG | CTT | TGC | TCC | CTA | GAA | GAA | GCT | CAA | AGG | ATA | 432 |
| Ser | Glu | Gly | Asn | Val | Lys | Leu | Cys | Ser | Leu | Glu | Glu | Ala | Gln | Arg | Ile | |
| | | 130 | | | | | 135 | | | | | 140 | | | | |
| TGG | AAA | CAA | AAG | TCG | GCA | GAG | ATT | TAT | CCA | ATA | ATG | GAC | AAG | TCA | AGC | 480 |
| Trp | Lys | Gln | Lys | Ser | Ala | Glu | Ile | Tyr | Pro | Ile | Met | Asp | Lys | Ser | Ser | |
| 145 | | | | | 150 | | | | | 155 | | | | | 160 | |
| CGC | ACA | CGT | CTT | GCT | CTC | ATT | ATC | TGC | AAT | GAA | GAA | TTT | GAC | AGT | ATT | 528 |
| Arg | Thr | Arg | Leu | Ala | Leu | Ile | Ile | Cys | Asn | Glu | Glu | Phe | Asp | Ser | Ile | |
| | | | | 165 | | | | | 170 | | | | | 175 | | |
| CCT | AGA | AGA | ACT | GGA | GCT | GAG | GTT | GAC | ATC | ACA | GGC | ATG | ACA | ATG | CTG | 576 |
| Pro | Arg | Arg | Thr | Gly | Ala | Glu | Val | Asp | Ile | Thr | Gly | Met | Thr | Met | Leu | |
| | | | 180 | | | | | 185 | | | | | 190 | | | |

Fig. 1

```
CTA CAA AAT CTG GGG TAC AGC GTA GAT GTG AAA AAA AAT CTC ACT GCT    624
Leu Gln Asn Leu Gly Tyr Ser Val Asp Val Lys Lys Asn Leu Thr Ala
        195             200             205

TCG GAC ATG ACT ACA GAG CTG GAG GCA TTT GCA CAC CGC CCA GAG CAC    672
Ser Asp Met Thr Thr Glu Leu Glu Ala Phe Ala His Arg Pro Glu His
210             215             220

AAG ACC TCT GAC AGC ACG TTC CTG GTG TTC ATG TCT CAT GGT ATT CGG    720
Lys Thr Ser Asp Ser Thr Phe Leu Val Phe Met Ser His Gly Ile Arg
225             230             235             240

GAA GGC ATT TGT GGG AAG AAA CAC TCT GAG CAA GTC CCA GAT ATA CTA    768
Glu Gly Ile Cys Gly Lys Lys His Ser Glu Gln Val Pro Asp Ile Leu
            245             250             255

CAA CTC AAT GCA ATC TTT AAC ATG TTG AAT ACC AAG AAC TGC CCA AGT    816
Gln Leu Asn Ala Ile Phe Asn Met Leu Asn Thr Lys Asn Cys Pro Ser
        260             265             270

TTG AAG GAC AAA CCG AAG GTG ATC ATC ATC CAG GCC TGC CGT GGT GAC    864
Leu Lys Asp Lys Pro Lys Val Ile Ile Ile Gln Ala Cys Arg Gly Asp
        275             280             285

AGC CCT GGT GTG GTG TGG TTT AAA GAT TCA GTA GGA GTT TCT GGA AAC    912
Ser Pro Gly Val Val Trp Phe Lys Asp Ser Val Gly Val Ser Gly Asn
290             295             300

CTA TCT TTA CCA ACT ACA GAA GAG TTT GAG GAT GAT GCT ATT AAG AAA    960
Leu Ser Leu Pro Thr Thr Glu Glu Phe Glu Asp Asp Ala Ile Lys Lys
305             310             315             320

GCC CAC ATA GAG AAG GAT TTT ATC GCT TTC TGC TCT TCC ACA CCA GAT   1008
Ala His Ile Glu Lys Asp Phe Ile Ala Phe Cys Ser Ser Thr Pro Asp
            325             330             335

AAT GTT TCT TGG AGA CAT CCC ACA ATG GGC TCT GTT TTT ATT GGA AGA   1056
Asn Val Ser Trp Arg His Pro Thr Met Gly Ser Val Phe Ile Gly Arg
        340             345             350

CTC ATT GAA CAT ATG CAA GAA TAT GCC TGT TCC TGT GAT GTG GAG GAA   1104
Leu Ile Glu His Met Gln Glu Tyr Ala Cys Ser Cys Asp Val Glu Glu
        355             360             365

ATT TTC CGC AAG GTT CGA TTT TCA TTT GAG CAG CCA GAT GGT AGA GCG   1152
Ile Phe Arg Lys Val Arg Phe Ser Phe Glu Gln Pro Asp Gly Arg Ala
        370             375             380

CAG ATG CCC ACC ACT GAA AGA GTG ACT TTG ACA AGA TGT TTC TAC CTC   1200
Gln Met Pro Thr Thr Glu Arg Val Thr Leu Thr Arg Cys Phe Tyr Leu
385             390             395             400

TTC CCA GGA CAT TAA                                                1215
Phe Pro Gly His
            405
```

Fig. 1 (continued)

Nucleic Acid Sequence for preIL-1β and Corresponding
Amino Acid Sequence

| | | | | | | | | | | | | |
|---|---|---|---|---|---|---|---|---|---|---|---|---|
| CTCGAGTCTG AAGCAGCC | ATG | GCA | GAA | GTA | CCT | GAG | CTC | GCC | AGT | GAA | ATG | 51 |
| | Met | Ala | Glu | Val | Pro | Glu | Leu | Ala | Ser | Glu | Met | |
| | 1 | | | | 5 | | | | | 10 | | |

ATG GCT TAT TAC AGT GGC AAT GAG GAT GAC TTG TTC TTT GAA GCT GAT    99
Met Ala Tyr Tyr Ser Gly Asn Glu Asp Asp Leu Phe Phe Glu Ala Asp
              15                  20                  25

GGC CCT AAA CAG ATG AAG TGC TCC TTC CAG GAC CTG GAC CTC TGC CCT   147
Gly Pro Lys Gln Met Lys Cys Ser Phe Gln Asp Leu Asp Leu Cys Pro
            30                  35                  40

CTG GAT GGC GGC ATC CAG CTA CGA ATC TCC GAC CAC CAC TAC AGC AAG   195
Leu Asp Gly Gly Ile Gln Leu Arg Ile Ser Asp His His Tyr Ser Lys
        45                  50                  55

GGC TTC AGG CAG GCC GCG TCA GTT GTT GTG GCC ATG GAC AAG CTG AGG   243
Gly Phe Arg Gln Ala Ala Ser Val Val Val Ala Met Asp Lys Leu Arg
60                  65                  70                  75

AAG ATG CTG GTT CCC TGC CCA CAG ACC TTC CAG GAG AAT GAC CTG AGC   291
Lys Met Leu Val Pro Cys Pro Gln Thr Phe Gln Glu Asn Asp Leu Ser
                80                  85                  90

ACC TTC TTT CCC TTC ATC TTT GAA GAA GAA CCT ATC TTC TTC GAC ACA   339
Thr Phe Phe Pro Phe Ile Phe Glu Glu Glu Pro Ile Phe Phe Asp Thr
            95                  100                 105

TGG GAT AAC GAG GCT TAT GTG CAC GAT GCA CCT GTA CGA TCA CTG AAC   387
Trp Asp Asn Glu Ala Tyr Val His Asp Ala Pro Val Arg Ser Leu Asn
        110                 115                 120

TGC ACG CTC CGG GAC TCA CAG CAA AAA AGC TTG GTG ATG TCT GGT CCA   435
Cys Thr Leu Asg Asp Ser Gln Gln Lys Ser Leu Val Met Ser Gly Pro
125                 130                 135

TAT GAA CTG AAA GCT CTC CAC CTC CAG GGA CAG GAT ATG GAG CAA CAA   483
Tyr Glu Leu Lys Ala Leu His Leu Gln Gly Gln Asp Met Glu Gln Gln
140                 145                 150                 155

GTG GTG TTC TCC ATG TCC TTT GTA CAA GGA GAA GAA AGT AAT GAC AAA   531
Val Val Phe Ser Met Ser Phe Val Gln Gly Glu Glu Ser Asn Asp Lys
                160                 165                 170

ATA CCT GTG GCC TTG GGC CTC AAG GAA AAG AAT CTG TAC CTG TCC TGC   579
Ile Pro Val Ala Leu Gly Leu Lys Glu Lys Asn Leu Tyr Leu Ser Cys
            175                 180                 185

Fig. 2

```
GTG TTG AAA GAT GAT AAG CCC ACT CTA CAG CTG GAG AGT GTA GAT CCC    627
Val Leu Lys Asp Asp Lys Pro Thr Leu Gln Leu Glu Ser Val Asp Pro
        190                 195                 200

AAA AAT TAC CCA AAG AAG AAG ATG GAA AAG CGA TTT GTC TTC AAC AAG    675
Lys Asn Tyr Pro Lys Lys Lys Met Glu Lys Arg Phe Val Phe Asn Lys
        205                 210                 215

ATA GAA ATC AAT AAC AAG CTG GAA TTT GAG TCT GCC CAG TTC CCC AAC    723
Ile Glu Ile Asn Asn Lys Leu Glu Phe Glu Ser Ala Gln Phe Pro Asn
220                 225                 230                 235

TGG TAC ATC AGC ACC TCT CAA GCA GAA AAC ATG CCC GTC TTC CTG GGA    771
Trp Tyr Ile Ser Thr Ser Gln Ala Glu Asn Met Pro Val Phe Leu Gly
                240                 245                 250

GGG ACC AAA GGC GGC CAG GAT ATA ACT GAC TTC ACC ATG CAA TTT GTG    819
Gly Thr Lys Gly Gly Gln Asp Ile Thr Asp Phe Thr Met Gln Phe Val
        255                 260                 265

TCT TCC TAAAGAGAGC TGTACGGATC C                                    846
Ser Ser
        270
```

Fig. 2 (continued)

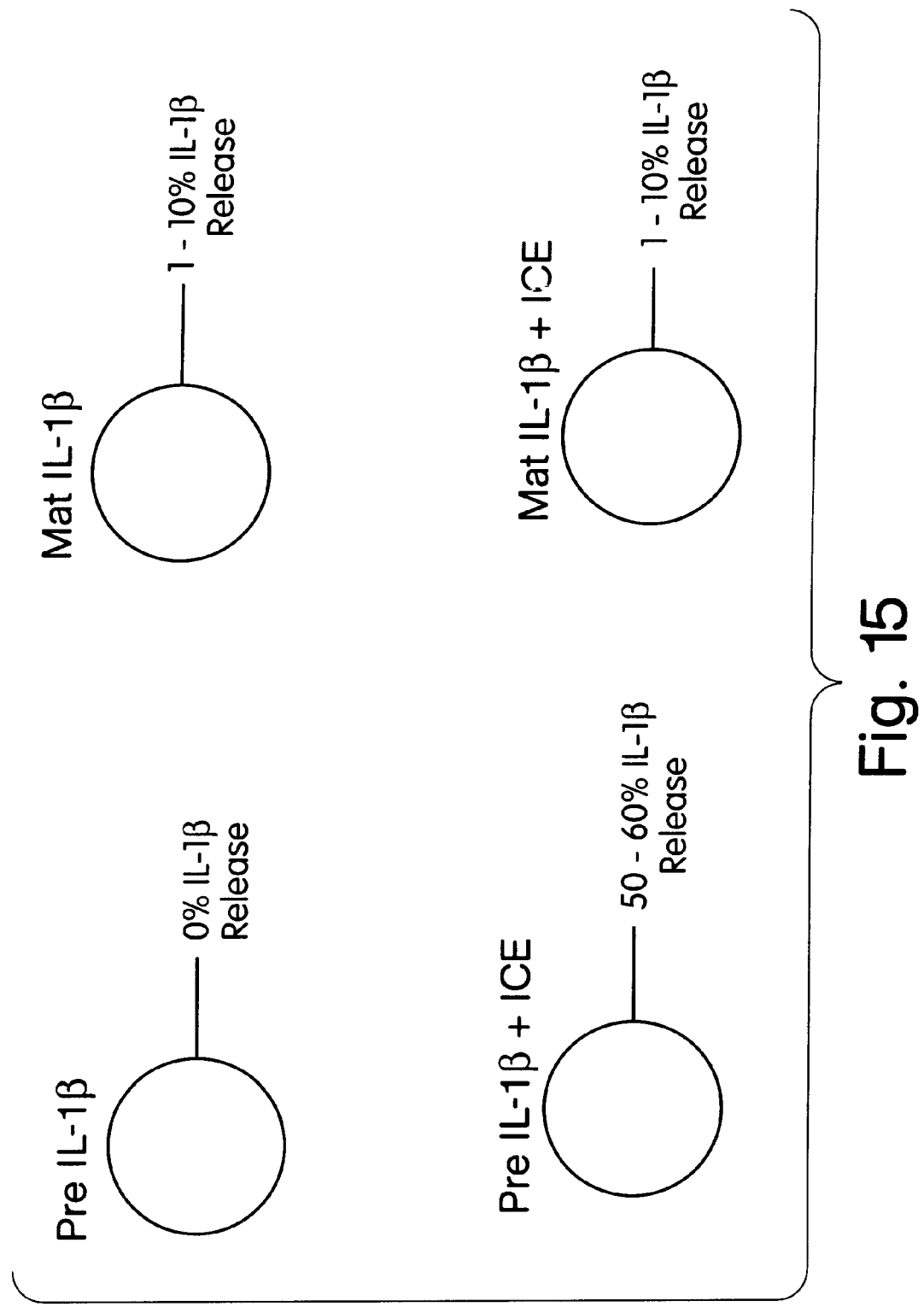

METHODS AND CELL LINES FOR SCREENING COMPOSITIONS AND GENES FOR ABILITY TO INTERACT WITH IL-1β AND ICE PROCESSING

This application is a continuation of application Ser. No. 08/280,889, filed on Jul. 27, 1994, now abandoned, entitled: METHODS AND CELL LINES FOR SCREENING COMPOSITIONS AND GENES FOR ABILITY TO INTERACT WITH IL-I β AND ICE PROCESSING. The contents of the aforementioned application is expressly incorporated by reference.

FIELD OF THE INVENTION

This invention features methods and non-naturally occurring cells for screening compositions and genes which interact with interleukin 1β and interleukin-1 beta converting enzyme (ICE) processing and/or activation.

BACKGROUND OF THE INVENTION

Interleukin-1 (IL-1) plays an important role in the pathogenesis of several inflammatory disorders. Two forms of IL-1 proteins have been described, interleukin-1-alpha (IL-1α) and interleukin-1-beta (IL-1β). This application will use the terms IL-1α and IL-1β to denote the respective forms of IL-1 proteins consistent with the usage of such terms in the scientific literature. See: Young et al. "Human Interleukin Ib is not secreted from Hamster Fibroblasts when expressed constitutively from transferred cDNA", *Journal of Cell Biology*, Vol. 107, 447–455 (1988). Both forms of IL-1 are synthesized as approximately 31 kDa precursor molecules that are subsequently processed to generate 17 kDa mature molecules. Although both forms of IL-1 are secreted proteins, each protein lacks signal peptides. The mechanism of the secretion has not been fully defined.

IL-1α and IL-1β are products of distinct genes. The proteins share only 27–33% of their amino acids even though each protein has a similar biological activity and interact with the same receptor. IL-1α precursor (preIL-1α) is almost as active as the mature form. In contrast, IL-1β precursor (preIL-1β) has no biological activity until further processed to a mature form. This application will use the term mature, bioactive IL-1β (matIL-1β) to highlight and emphasize that a precursor composition has been processed to the mature, active composition. In humans, IL-1β is the predominant species and may play a more important role in certain disease states.

Only certain cell types process preIL-1β and secrete matIL-1β. Monocytes and macrophages are the most efficient producers and secretors of IL-1β. Of the two forms of IL-1 synthesized and secreted following activation of monocytes and macrophages, IL-1β is the most abundant form.

The cellular processing of preIL-1β to mature, bioactive IL-1β is mediated by the enzyme ICE, a cysteine protease. ICE is synthesized as a 45 kDa precursor molecule which is processed in vivo to form fragments of 20 and 10 kDa. These two fragments are combined or folded, in vivo, to form the active enzyme.

IL-1β plays a critical role in the pathogenesis of several inflammatory, autoimmune, and leukemic disease states. Thus, an understanding of the release and processing of IL-1β and its precursors is desired. The present knowledge is, in part, limited by a lack of models on the cellular level for the making and processing of IL-1β. In vivo, at the cellular level, monocytes and macrophages produce small quantities of IL-1β, for only a limited time. It is difficult to grow monocytes and macrophages for long periods of time. There are large differences and variations between freshly prepared monocytes and macrophages. In naturally occuring cells, it is difficult to study preIL-1β and ICE interactions. As a consequence, the role of various regions or domains of preIL-1β and ICE in the processing, activation and release of ICE and IL-1β, and the structural significance of various amino acid residues remain unclear.

A consistent model capable of alteration and manipulation is desired to further the understanding of the release and processing of IL-1β and ICE and as a screen for compositions which may interact with the processing and release of IL-1β and ICE. A consistent model that mimics the induction of preIL-1β upon the application of a stimulus, and consistently expresses ICE, is desired.

Compositions which alter the production, processing and release of IL-1β and ICE have interest as therapeutics to modulate the inflammation response. IL-1β and ICE themselves may also have utility to modulate inflammatory responses.

SUMMARY OF THE INVENTION

The present invention is directed to methods and cell lines for screening compositions and genes for ICE activity or ICE inhibitory or agonist activity. One embodiment of the present invention features a non-naturally occurring cell which cell stably incorporates a gene for preIL-1β operably linked to a promoter. The cell produces preIL-1β, but, in the absence of ICE, is unable to process preIL-1β to make mature, bioactive IL-1β. A cell having a gene for preIL-1β operably linked to a promoter has utility to identify nucleic acids coding ICE or ICE-like compositions and to identify ICE-like compositions which can be applied directly to the cell.

The term "non-naturally occurring" refers to an object which has been manipulated or changed from its natural state. As applied to a cell, a non-naturally occurring cell has a non-naturally occurring nucleic acid, or makes a non-naturally occurring peptide, or is fused to a cell to which it is not combined with in nature. The term "non-naturally occurring nucleic acid" refers to a portion of a genomic nucleic acid, cDNA, semisynthetic nucleic acid, or synthetic original nucleic acid which, by virtue of its origin or manipulation, is not associated with all of a nucleic acid to which it is associated in nature, or is linked to a nucleic acid or other chemical agent other than that to which it is linked in nature, or does not occur in nature. The term "non-naturally occurring peptide" refers to a portion of a larger naturally occurring peptide or protein, or semisynthetic or synthetic peptide, which by virtue of its origin or manipulation, is not associated with all of the peptide to which it is associated in nature, or is linked to a peptide, functional group or chemical agent other than that to which it is linked in nature, or does not occur in nature.

As used herein, the term "operably linked" refers to a nucleic acid which is associated in a manner to effect transcription and translation by a cell in which it is placed.

The term "stably incorporated" refers to maintaining a feature or gene through several cell divisions.

The term "unable to process preIL-1β" refers to a substantial absence of mature, bioactive IL-1β in the presence of preIL-1β. A substantial absence of mature bioactive IL-1β is less than 5–10% of total preIL-1β protein.

As used herein, "ICE" refers to IL-1β converting enzyme as defined in European Patent Application No. 92307479.3 having a filing date of Aug. 14, 1992, by Merck & Company, Inc. ICE-like compositions refers to molecules and compositions which have ICE activity, that is, which function to convert the 31 kDa precursor protein, preIL-1β, into a 17 kDa mature bioactive IL-1β molecule. By way of example, without limitation, such ICE-like molecules comprise separately expressed 10 and 20 kDa fragments, recombinant ICE, fragments derived from the 45 kDa preICE molecule (including but not limited to a 32 kDa fragment) and proteins resembling ICE with non-critical amino acid substitutions, deletions and additions. Separately expressed fragments and recombinant ICE further comprise such additional amino acids which are added to mammalian proteins when nucleic acid coding such proteins is expressed in bacterial systems and restriction sites and other features, which permit cloning.

Preferably, the cell has a gene for preIL-1β stably incorporated within its genome. Such cell is a model cell for a cell which does not process and secrete preIL-1β. A preferred cell line comprising cells designated COS pre 11 has been deposited with the American Type Culture Collection (ATCC) of Rockville, Md. on Jul. 27, 1994 under the terms of the Budapest Treaty and in accordance with U.S. Patent Practice. This cell-line has the ATCC designation of Accession No. CRL 11693.

One embodiment of the present invention comprises the step of applying preICE, ICE, ICE-like compositions and other compositions which are to be evaluated for activity in forming mature, bioactive IL-1β to a cell having a gene for preIL-1β operably linked to a promoter. Further, genes for such compositions operably linked to a promoter can be placed in such cells to evaluate the nucleic acid and the compositions encoded by such nucleic acid for ICE activity. Upon imposition of conditions for transcription and translation the cell makes preIL-1β and ICE, preICE, ICE-like compositions and such other compositions. The cells or the environment surrounding the cells are monitored for the formation of mature, bioactive IL-1β. The formation of mature, bioactive IL-1β is indicative of a composition that is ICE, preICE or is ICE-like in function or which is a nucleic acid coding ICE, preICE or a ICE-like composition.

As used herein, the term "applying" is used in the sense of placing within or near, for example, such that a cell may receive and interact with that which is being applied.

As used herein, the term "environment surrounding the cell", refers to an area in which cellular secretions are likely to be found, such as the supernatant fluid or culture media in which a cell is found or grown. The term, "monitoring the cell or the cell environment" refers to examining or evaluating the cell constituents in vivo or in vitro, including lysates of the cell and the cellular constituents or examining the cell environment.

Cells which have genes for preIL-1β or IL-1β operably linked to a promoter and which have received preICE, ICE or ICE-like compositions, or genes for such compositions operably linked to a promoter, are appropriate models for naturally occurring cells which process and secrete bioactive IL-1β. A further embodiment of the present invention features a non-naturally occurring cell having a gene encoding preIL-1β operably linked to a promoter and one or more genes coding preICE, ICE or ICE-like compositions operably linked to one or more promoters. The cell expresses the gene coding preIL-1β to produce preIL-1β. The cell also expresses one or more genes for preICE, ICE or ICE-like compositions, which preICE or ICE-like compositions are processed by the cell to make ICE or compositions which function as ICE. The cell processes preIL-1β with the ICE or ICE-like compositions to make IL-1β.

Such cells are useful for initiating an inflammation response in the event such cells are made and transported into a subject. Such cells, as models for IL-1β processing by ICE, are also useful for identifying compounds or compositions having ICE agonist or ICE inhibitory actions or compositions which interact with ICE or IL-1β processing and secretory pathways. As used herein, the term "subject" refers to an individual or an animal receiving such cell, or a composition which interacts with ICE or IL-1β secretory pathways as a therapeutic aid or as a diagnostic test.

One embodiment of the present invention features a method of screening compositions for ICE inhibitory or ICE agonist action. The method comprises the steps of applying a composition to a non-naturally occurring cell which cell has a gene coding preIL-1β operably linked to a promoter. The cell also has one or more genes for preICE, ICE or ICE-like compositions, each of such one or more genes also operably linked to a promoter. The cell is capable of expressing the preIL-1β gene and the one or more genes for preICE, ICE or ICE-like compositions. The preICE or ICE-like compositions are processed, if necessary, to form bioactive, mature ICE or ICE-like compositions. The preIL-1β is processed by ICE and ICE-like compositions to form IL-1β in the absence of inhibitory compositions. The method further comprises the step of monitoring the cell or the environment which surrounds the cell for the presence of IL-1β. The presence of IL-1β is indicative of a composition without inhibitory action and, if present in concentrations greater than similar cells, which similar cells did not receive an application of the composition to be evaluated, is indicative of ICE agonist activity. The absence of IL-1β or the presence of IL-1β in concentrations less than similar cells, which similar cells did not receive an application of the composition to be evaluated, is indicative of a composition having inhibitory action.

Preferably, the cell is a member of a cell culture which cell culture can be monitored en masse. Preferably, the cell does not naturally express at least one, but preferably, both genes encoding preIL-1β or mature bioactive IL-1β and genes encoding ICE, preICE and ICE-like compositions.

Preferably, cells expressing ICE, preICE or ICE-like composition genes are not subject to apoptosis. A preferred cell is a Chinese hamster ovary (CHO) cell, CV-1 cell, mouse NIH-3T3 cell, or monkey epithelial kidney cell. A particularly preferred cell, capable of culture, is a monkey epithelial kidney cell, for example, without limitation a COS-1 cell. Cos-1 cells carry an antiapoptosis gene. A preferred cell, expressing a gene for ICE and preIL-1β, is clone Pre+1 #58 ("clone #58"), deposited with the American Type Culture Collection, Rockville, Md. on Jul. 27, 1994 in accordance with the Budapest Treaty. This deposit has the ATCC deposit designation of Accession No. CRL 11696 A preferred cell expressing a gene for an ICE-like composition is ICE clone 1 #6 (also referred to herein as "ICE p45") described in Table 8, deposited with the American Type Culture Collection, Rockville, Md. on Jul. 27, 1994 in accordance with the Budapest Treaty. This deposit has the the ATCC deposit designation of Accession No. CRL 11695 A further preferred cell line for use as a counter-screen, stably expressing genes for matIL-1β and p45 ICE, is clone Mat+Cl.1 #10 ("clone #10"), deposited with the American Type Culture Collection, Rockville, Md. on Jul. 27, 1994 in accordance with the Budapest Treaty. This deposit has the ATCC deposit designation of Accession No. CRL 11694. Finally, a preferred COS cell line expressing preIL-1β is clone COS pre 11, deposited with the American Type Culture Collection, Rockville, Md. on Jul. 27, 1994 in accordance with the Budapest Treaty. This deposit has the ATCC deposit designation of Accession No. CRL 11693.

Preferably cells expressing a gene for ICE, preICE or an ICE-like composition are maintained at temperature of 37° C. or less than 37° C. A preferred temperature range for performing screening with such cells is 27°–37° C. and, more preferably, 29° to 35° C., and, most preferably, 31° to 33° C.

Preferably, the one or more genes for preICE, ICE or ICE-like compositions comprise a gene encoding a 20 kDa fragment and a gene encoding a 10 kDa fragment. The 20 kDa fragment and 10 kDa fragment are capable of being refolded in vivo to form an active ICE or ICE-like molecule.

One embodiment of the present invention comprises a non-naturally occurring cell having a gene for a preICE, ICE or ICE-like composition operably linked to a promoter. Such cells are useful for making quantities of ICE, preICE or ICE-like compositions. Preferably such non-naturally occuring cell has an antiapoptosis gene, to allow such cell to express ICE, preICE or ICE-like compositions.

A further embodiment of the present invention comprises a method of making a non-naturally occurring ICE, preICE, or ICE-like composition and the products formed. One such non-naturally occurring ICE, preICE, or ICE-like composition is the product of a gene for a first fragment of the two fragments which comprise ICE or an ICE-like composition and a second gene for the second fragment of ICE or an ICE-like composition. In vitro, the separately expressed fragments are folded and combined to form ICE or an ICE-like composition.

A further composition of the present invention features a protein having the amino acid sequence of SEQ ID NO. 1, wherein at the 297 amino acid position, the amino acid aspartate is mutated, preferably to alanine. This composition does not undergo autocatalysis to form a p20 and p10 ICE-like composition. The p32 composition acts as ICE to process preIL-1β to make IL-1β. A further embodiment of the present invention is a cell which makes ICE, preICE or ICE-like compositions.

A further embodiment of the present invention features a method of screening compositions for activity within the ICE or IL-1β metabolic pathway. One method features applying a composition to a non-naturally occuring cell. The cell has one more gene encoding preIL-1β or matIL-1β, which gene is operatively linked to a promoter. The cell further has one or more genes for preICE, ICE or an ICE-like composition which one or more genes are operably linked to a promoter. The cell expresses the one or more preIL-1β or matIL-1β genes and the one or more preICE, ICE or ICE-like composition genes, to process preICE and, if necessary, ICE-like compositions to form ICE or an active ICE-like composition. The ICE and active ICE-like composition process preIL-1β to form IL-1β and participate in secretion events to secrete matIL-1β in the absence of inhibiting compositions. The cell environment is monitored for the presence of matIL-1β. The different levels of IL-1β may indicate compositions which act as agonists or inhibitors of the production, processing and secretion of IL-1β and its precursors and ICE and its precursors.

A preferred method screens compositions which interact with the secretory pathway of IL-1β. Compositions may interfere with the secretion of matIL-1β without interacting with the active site of ICE.

Preferably, the cells have the features previously described. Cells which express ICE, preICE or ICE-like compositions preferably have a gene for an antiapoptosis composition. Preferably, the cells are maintained in a preferred temperature range of 27°–37° C. and more preferably, 29°–35° C., and most preferably, 31°–33° C. COS-1 cells express an antiapoptosis composition and are a preferred cell.

A further embodiment of the present invention features a method of inhibiting the secretion of preIL-1β and IL-1β from cells. The method comprises the steps of applying an inhibitory composition to a cell expressing one or more genes for preIL-1β or IL-1β and one or more genes for ICE, preICE or an ICE-like composition. The inhibitory composition binds to the prodomain of preIL-1β or binds to a non-active site of ICE, or an ICE-like composition, in an area of ICE or such ICE-like composition which binds the prodomain of IL-1β preventing processing of preIL-1β and secretion of preIL-1β or matIL-1β.

Embodiments of the present invention further feature inhibitory compositions which bind to the prodomain of preIL-1β or in an area of ICE or an ICE-like composition which interacts with the prodomain of preIL-1β.

As used herein, the term "prodomain of preIL-1β" refers to that part of preIL-1β which is cleaved and separated from the preIL-1β to form matIL-1β. The prodomain of preIL-1β corresponds to amino acids 1–116 of preIL-1β. Such compositions which bind to the prodomain of preIL-1β or an area of ICE or an ICE-like composition which binds the prodomain of preIL-1β are antibodies or other low molecular weight chemical entities.

ICE and ICE-like compositions are apoptotic, causing or promoting cell death. Cells which express ICE and ICE-like compositions are useful in identifying compositions which interact with apoptosis pathways. One embodiment of the present invention features a method of identifying compositions which interact with the apoptosis pathways and compositions so identified.

One method comprises the step of applying a composition to be evaluated to a cell. The cell has a gene encoding an apoptotic composition operably linked to a promoter. Upon imposition of expression conditions, the cell expresses such apoptosis gene. The cell is monitored for cell death. Compositions which prevent cell death suggest the composition may have antiapoptosis effects.

Preferably, the gene comprises a gene encoding ICE, preICE or an ICE-like composition. Preferably, the cell has one or more genes for an antiapoptosis composition operatively linked to a promoter. Upon imposition of expression conditions, the cell makes an apoptosis composition and an antiapoptosis composition. Viable cells have a balance of the conflicting compositions. The cell is monitored after the application of a composition to be evaluated and the imposition of expression conditions. Cells which die under such conditions suggest a composition which has antiapototic effects, as an agonist of ICE or apoptotic or ICE-like protein, or as an inhibitor/antagonist of the antiapoptosis gene or composition.

Preferably, the gene which encodes an apoptotic composition encodes ICE, preICE or an ICE-like composition. Preferably, the gene which encodes an antiapoptotic composition encodes Bcl-2, Bcl-X, ced-9, P35 or Bax.

Individuals skilled in the art will readily recognize one or more cells of the present invention can be packaged with instructions, in the form of a kit, for screening compositions for ICE inhibitory or agonist activity or for identifying compositions or nucleic acids coding such compositions having ICE activity. Such kits would normally be comprised of a suitable containment vessel holding the one or more cells, reagents, media and the like with instructions and packaging.

Individuals skilled in art will readily recognize that compositions identified as possessing ICE agonist or ICE inhibitory action have therapeutic utility for treating subjects having diseases characterized by an inappropriate immune response. As used herein, an inappropriate immune response refers to an insufficient immune response or an immune response which is damaging to the subject such as, without limitation, autoimmune diseases such as rheumatoid arthritis, some cancers, some diabetic conditions, endotoxic shock, transplant rejection and the like.

The present invention provides methods of using therapeutic compositions comprising an effective amount of non-naturally occurring ICE-like compositions, or an ICE agonist, or ICE inhibiting composition, or an antiapoptosis composition, or an apoptosis composition and derivatives thereof in a suitable diluent and carrier. For therapeutic use, a composition identified as having ICE agonist or inhibitory action or ICE activity, or antiapoptosis activity or apoptosis activity is administered to a subject, preferably a human, for treatment in a manner appropriate to the indication. Thus, for example, a composition administered to suppress autoimmunity can be given by bolus injection, continuous infusion, sustained release from implants, or other suitable technique. Typically, the composition will be administered in the form of a pharmaceutical formulation comprising the composition in conjunction with physiologically acceptable carriers, excipients or diluents. Such carriers will be nontoxic to patients at the dosages and concentrations employed and can contain any of the conventional excipients utilized to prepare pharmaceutical formulations.

The ICE inhibitory compositions of the present invention are useful in inhibiting the physiological actions of IL-1β by preventing formation or secretion of biologically active IL-1β. The inhibition of preIL-1β processing results in a decrease in active IL-1β levels and a concomitant increase in preIL-1β, which protein is biologically inactive.

The agonist compositions of the present invention are also useful in treating dysfunctional states mediated by decreased IL-1 activity.

Mammals needing treatment for an inflammatory disorder or prevention of an autoimmune condition are administered effective amounts of a composition of this invention either alone or in the form of a pharmaceutical formulation.

The compositions of the present invention are combined with one or more non-toxic physiologically acceptable carriers, adjuvants or vehicles which are collectively referred to herein as carriers, for parenteral injection, for oral administration or solid or liquid form, for rectal or topical administration, and the like.

The total daily dose of the composition of this invention administered to a subject in single or divided doses may be in amounts, for example, of from about 0.1 mg to about 160.0 mg per kilogram of body weight. Dosage unit compositions may contain such amounts or such submultiples thereof as may be used to make up the daily dose. The specific dose level for any particular patient will depend upon a variety of factors including the body weight, general health, sex, diet, time and route of administration, rates of absorption and excretion, combination with other drugs and the severity of the particular disease being treated.

The present invention is further described in the following figures which illustrate features of the present invention and the following examples which highlight preferred embodiments and the best mode to carry out features of the present invention.

BRIEF DESCRIPTION OF THE DRAWINGS

FIG. 1 depicts the nucleotide sequence and the amino acid sequence corresponding to a 45 kDa protein preICE, also set forth as SEQ ID NO. 1 and SEQ ID NO. 2, respectively;

FIG. 2 depicts the nucleotide sequence and the amino acid sequence of a protein corresponding to preIL-1β also set forth as SEQ ID NO. 3 and SEQ ID NO. 4, respectively;

FIG. 15 is an illustration depicting summary of IL-1β release of various single and double stable COS cells;

DETAILED DESCRIPTION OF THE INVENTION

Figure 3:
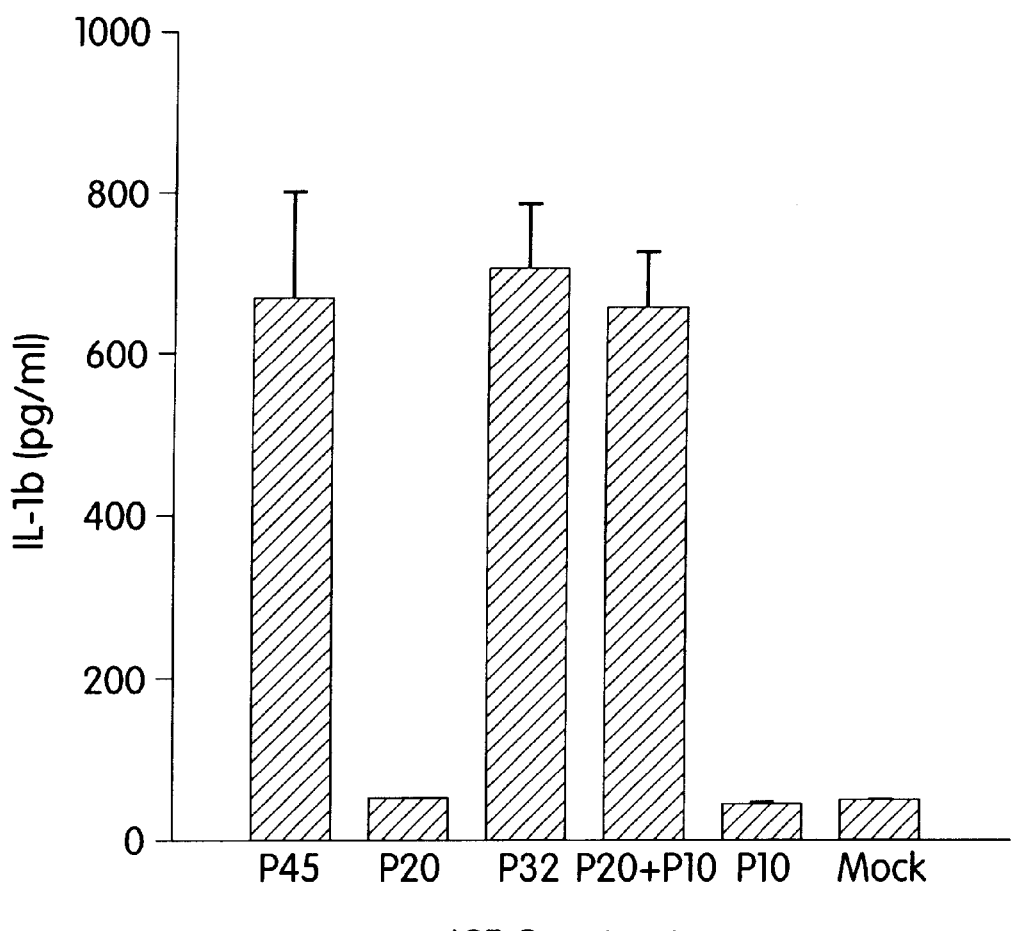
FIG. 3 depicts in bar graph form the production and secretion of IL-1β (as determined by ELISA) into a supernatant by cells having a gene for preIL-1β operably linked to a promoter which cells are transiently transfected with genes for ICE, preICE and ICE-like compositions.

The present invention will be described in detail as methods and cell lines for screening genes and compositions for ICE activity, ICE agonist and inhibitory activity; and for screening genes and compositions for apoptosis activity; for antiapoptosis activity; and for screening for inhibitors of IL-1β and ICE secretory pathways.

The practice of the present invention will employ, unless otherwise indicated, conventional techniques of chemistry, molecular biology, microbiology, recombinant DNA technology and immunology, which are within the skill of the art and are explained fully in the literature. See, e.g., Sambrook, Fritsch and Maniatis, *Molecular Cloning*: Cold Spring Harbor Laboratory Press (1989); *DNA Cloning*, Vols. 1 and 2, (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); the series *Methods In Enzymoloqy* (Academic Press, Inc.), particularly Vol. 154 and Vol. 155 (Wu and Grossman, Eds.).

Other features of the invention will be apparent from the following examples.

EXAMPLES

Example 1

General Methods and Materials

A. Cell Culture

THP. 1 cells were obtained from American Type Culture Collection and cultured in complete media (RPMI-1640 supplemented with 10% FCS (Sigma, St. Louis, Mo.), penicillin (50U/ml), streptomycin (50 ug/ml) and L-Glutamine (290 ug/ml)(GIBCO, Grand Island, N.Y.), at a concentration of $3 \times 10^6$ cells/ml and stimulated with 3 ug/ml of LPS (*E. coli* 0111:B4, Calbiochem, La Jolla, Calif.) for a period of 18 hrs.

B. Isolation of mRNA and First Strand cDNA Synthesis mRNA was isolated from LPS stimulated THP.1 cells using a FastTrack mRNA isolation Kit (Invitrogen, San Diego, Calif.). First strand cDNA synthesis was carried out from oligo dT primed mRNA using the Librarian Kit (Invitrogen, San Diego, Calif.). This single stranded cDNA was used as template in a polymerase chain reaction (PCR) to clone both the precursor IL-1β and the p45 form of precursor ICE (preICE).

C. Polymerase Chain Reaction (PCR)-Cloning

1. PCR Conditions

To amplify the full length preIL-1β and the p45 preICE cDNAs for unidirectional cloning, appropriate 5' and 3' primers (1 uM of each), and AmpliTag polymerase (Perkin Elmer Cetus) were mixed with single stranded THP.1 cDNA (5ng). The conditions for PCR were: denaturation 94° C. for 1.5 min; renaturation 55° C. for 2.5 mins; and amplification 72° C. for 4 minutes with the final extension lengthened to 10 mins.

2. Cloning of Precursor IL-1β

PCR-primers were designed based upon the published cDNA sequence of preIL-1β (Ref: Auron, P. E., et al., 1984 *PNAS (USA)* 81:7907; and March, C. J. et al., 1985 *Nature* 315:641). These primers were designated ILP1, ILP2, and ILP3 and are set forth in Table 1 below.

TABLE 1

ILP1; 5'→3':
CCCCTCGAGTCTGAAGCAGCCATGGCAGAAGTACCT (Xho 1 5')

ILP2; 5'→3':
CCCGGATCCGTACAGCTCTCTTTAGGAAGACACAAA (BamH1 3')

TABLE 1-continued

ILP3; 5'→3':
CCCATGCATGGAAGACACAAATTGCATGGTGAAGTC (Nsi-1 3')

The 5' primer, ILP1, contained a Xho1 restriction site. Primer ILP1 is set forth as SEQ ID NO. 5. The 3' primer, ILP2, and contained a BamH1 restriction site. Primer ILP2 is set forth as SEQ ID NO. 6. The primer ILP3 contained a NSI-1 restriction site. Primer ILP3 is set forth as SEQ ID NO. 7. The preIL-1β PCR products were purified using GeneClean (Bio 101 Inc.) and the Xho1/BamH1 product was subcloned into the transient expression vector pKV. The Xho1/NSI1 preIL-1β PCR product was subcloned into MNC vector for the generation of preIL-1β stable cell lines.

P45 and p32 ICE PCR-Products were also subcloned into the MNC vector to generate ICE single stable cell lines and ICE and preIL-1β double stable cell lines. The MNC vector, although generally available, was kindly provided by Dr. B. Seed of Massachusetts General Hospital of Cambridge, Mass.

3. Cloning of ICE, preICE and ICE-like Compositions

Nucleic acids encoding ICE, preICE and ICE-like compositions were constructed with the use of PCR. PCR-primers were designed based upon the published preICE cDNA sequence which is set forth in SEQ ID NO. 1 and FIG. 1.

Primers for the synthesis of ICE, preICE and ICE-like compositions are set forth in Table 2 below:

TABLE 2

ICP1; 5'→3':
CCCCTCGAGGCCATGGCCGACAAGGTCCTGAAGGAG (Xho 1 5')

ICP2; 5'→3':
CCCCTCGAGATGAACCCAGCTATGCCCACATCCTCA (Xho 1 5')

ICP3; 5'→3':
CCCGGATCCTTAATCTTTAAACCACACCACACCAGG (BamH1 3')

ICP4; 5'→3':
CCCCTCGAGATGGCTATTAAGAAAGCCCACATAGAG (Xho 1 5')

ICP5; 5'→3':
CCCGGATCCATTTTAATGTCCTGGGAAGAGGTAGAA (BamH1 3')

Primers ICP1, ICP2, ICP3, ICP4 and ICP5 are disclosed as SEQ ID NO. 8, SEQ ID NO. 9, SEQ ID NO. 10, SEQ ID NO. 11 and SEQ ID NO. 12, respectively.

A nucleic acid corresponding to a 32 kDa ICE-like composition (p32) was constructed with PCR using primers ICP2 and ICP5. This ICE-like composition, p32, corresponds to amino acids 120–404 of the full 45 kDa preICE molecule set forth in SEQ ID NO. 2 and FIG. 1. An initiation codon for methionine was added to the sequence.

A nucleic acid corresponding to a 20 kDa ICE-like (p20) composition was constructed with PCR using primers ICP2 and ICP3. This ICE-like composition, p20, corresponds to amino acids 120–297 of the full 45 kDa preICE molecule set forth in SEQ ID NO. 2 and FIG. 1. An initiation codon for methionine was added to the sequence.

A nucleic acid corresponding to a 10 kDa ICE-like composition was constructed with PCR using primers ICP3 and ICP4. This ICE-like composition, p10, corresponds to amino acids 317–404 of the full 45 kDa preICE molecule, set forth in SEQ ID NO. 2 and in FIG. 1. An initiation codon for methionine was added to the sequence.

For cloning of the 45 kDa protein corresponding to preICE, amino acids 1–404 of SEQ ID NO. 2, 5' and the 3' primers, ICP1 and ICP5, were used.

These primers contain a Xho1 and BamH1 restriction sites respectively. The ICE PCR products were purified by GeneClean (Bio 101 Inc.) and subcloned into a transient expression vector, or MNC vector for stable expression of such cDNAs.

A full length ICE precursor (p45) cDNA was subcloned into a transient expression vector and used as a template to PCR-clone the p32, p20, and p20 ICE forms. All the ICE PCR products obtained were purified using GeneClean (Bio 101 Inc.) and subcloned undirectionally into an SV40-driven transient expression plasnid, or into MNC vector for stable expression of these DNAs.

4. Cloning of Precursor IL-1β Mutant

A mutant form of preIL-1β was generated by site directed mutagenesis. The ICE cleavage site Asp 116—Ala 117 in preIL-1β was mutated to Asn 116—Val 117 in the mutant, It has been suggested that such a mutant would not be cleaved by ICE. Ref: Sleath, P. R., et al., 1990 *J. Biol. Chem.* 265:14526.

Briefly, to make the mutant form of the preIL-1β, two internal overlapping oligonucleotides primers, mutant-5', MP2, and mutant 3' MP3, were designed such that they each contained site specific mutations, six altered nucleotides. These site specific mutations were flanked by homologous sequences from preIL-1β. These primers, MP2 and MP3, with the six altered nucleotides highlighted with underlining, are set forth below in Table 3 and set forth as SEQ ID NO. 13 and SEQ ID NO. 14, respectively.

TABLE 3

MP2; 5'→3':
GATAACCAGGCTTATGTGCAC<u>AACGTC</u>CCTGTACGATCACTGAACTGC

MP3; 5'→3':
GCAGTTCAGTGATCGTACAGG<u>GACGTT</u>GTGCACATAAGCCACGTTATC

Using the preIL-1β containing PkV plasmid as the PCR template, the MP2 and ILP4 primers were used to synthesize the 3'-mutant gene fragment. Similarly, the ILP1 and MP3 primers were used to synthesize the 5'-mutant gene fragment. The PCR fragments from the above two reactions were purified by GeneClean (Bio101 inc) and were then combined in an equal molar ratio to carry out overlap extension PCR. The extension reaction generated the assembled preIL-1β mutant gene which was subsequently amplified using the ILP1 and ILP2 primers.

The 5' and 3' preIL-1β primers that were used to generate the preIL-1β mutant, were identical to those used to clone preIL-1β, namely, ILP1 and ILP2 (Table 2). Such primers contain Xho1/BamH1 restriction site adaptors necessary for unidirectional cloning into transient expression plasmid. Furthermore, the MP2 and MP3 primers described in Table 3 were designed such that the codon used to represent the mutated amino acids introduced one unique restriction enzyme site, such as, Mae 11 and Fin 1. This enabled a fast determination of the fidelity of the generated mutants. The preIL-1β mutant PCR product was purified by GeneClean and subcloned into the transient expression plasmid, PKV.

D. Generation of ICE Mutants

This example sets forth a protocol for the generation of a Cys 285 ICE mutant and an Asp 297 Mutant.

For Cys 285->Ser point mutation the primers used are set forth in Table 4 below and as SEQ ID NO, 15 and SEQ ID NO. 16, respectively:

TABLE 4

Ser P1; 5'→3':
CGAAGGTGATCATCATCCAGGCCTCCCGTGGTGACAGCCC

Ser P2; 5'→3':
GAGGCCTGGATGATGATCACCTTCGGTTTGTCCTTCAAAC

For Cys 285->Ala point mutation the primer used is set forth in Table 5 below and as SEQ ID NO. 17:

TABLE 5

Ala P1; 5'→3':
CATCATCCAGGCCGCCCGTGGTGACAGCCC

The PCR reaction was set up using 1–5 ng of circular plasmid under the following conditions: 95° C. for 5 sec.; 52° C. for 20 sec.; 72° C. for 5 minutes for 25 cycles. The primers used were 40b each with 25b overlap (-15b extended in 3' direction). The mutation lies at the extreme 5' end of one primer and therefore—25b from the 5' end of the other primer. This setup produces a PCR product that contains the desired mutation as well as complementary ends. The ends recombine in vivo after transformation into HB 101. The PCR product was gel purified by GeneClean prior to transformation. The transformed HB 101 was plated out on LB ampicillin plates. Five colonies were selected, plasmids subjected to restriction enzymes and nucleic acids sequenced.

The Cys 285->Ala mutant plasmid in the p32 form of ICE was used as a template to generate the p20 Cys 285->Ala ICE mutant form using primers ICP2 and ICP3 as shown in Table 2. The preIL-1β, ICE-like compositions, the preIL-1β mutant, and the Cys 285 ICE mutants generated by PCR were sequenced before use.

Using the same protocol but with different primers, an Asp 297->Ala mutant was produced. These mutant primers are set forth in Table 6 below and as SEQ ID NO. 18 and SEQ ID NO. 19, respectively:

TABLE 6

Ala P1; 5'→3':
GCCCTGGTGTGGTGTGGTTTAAAGCTTCAGTAGGAGTTTC

Ala P2; 5'→3':
GCTTTAAACCACACCACACCAGGGCTGTCACCACGGCAGG

E. Generation of preIL-1β Stable COS Cell lines and other Stable Cell Lines

Twenty-four hours prior to transfections, COS cells were plated at a density of $10^6$ cells/100 mm/dish in complete media (DMEM, Gibco, Grand Island, N.Y.) supplemented with 10% FCS, penicillin, streptoeycin and L-glutamine) and incubated at 37° C. and 5% $CO_2$. Media was changed prior to transfection with a final volume of 6 ml/dish 30 ug total DNA, was precipitated and resuspended in 1 ml Hank's Balanced Salt Solution (HBSS). To form $CaPO_4$ precipitate, 60 ul of 2.5M $CaCl_2$ was added to DNA/HBSS solution and left at room temperature for 15 minutes . The DNA solution was added to the cells and left at room temperature for 20 minutes. Cells were then incubated for 4 hours at 37° C. and 5% $CO_2$. Cells were shocked with 5 ml of 15% glycerol/HBSS for 2 minutes at room temperature, rinsed 2x with media and incubated in complete DMEM media overnight. The next day, media was changed and on the third day, cells were split into complete media containing G418 (500 uq/ml). Media was changed every 2–3 days and colonies appeared after 7–10 days which were cloned at day 14 post transfection.

COS cells stably incorporating genes for preIL-1β or matIL-1β, COS cells stably incorporating genes for preICE, ICE and ICE-like compositions and COS cells incorporating genes for preIL-1β or matIL-1β and ICE, preICE and ICE-like compositions were made.

F. Transfections in COS cells

Cells, COS preIL-1β or COS cells, were plated in 100 mm dishes, to a density of approximately 1–4×10$^6$ cell, 24 hours prior to transfections. These plated cells were transfected with 10 μg of each plasmid. Cells were washed twice with PBS and 4 ml of DNA-DEAE mix (1.25–10 ug of DNA in 0.5 mg/ml DEAE Dextran (Pharmacia, Piscaway, N.J.)). PBS was then added to cells for 30 minutes at 37° C. Following this incubation, 8 ml of an 80 uM solution of chloroquine in serum free media was added to the cells for 2½ hours at 37° C. Media was aspirated and 8 ml of 10% DMSO in serum free media was added for 2 minutes. Cells were washed with serum free media and fresh complete DMEM media was added. Supernatants and cell lysates were collected at 24 and 48 hours post transfections.

G. IL-1β Determinations

1. IL-1β ELISA

The human IL-1β ELISA kit was purchased from R&D systems (Minneapolis, Minn.) and used according to its specifications. The limit of detection of this kit is between 5–10 pg/ml and can detect both the mature IL-1β and the denatured precursor form of human IL-1β.

2. The D10 Bioassay

D10G4.1 cells were used 2 days after IL-2 stimulation and plated at 10$^4$ cells/well in 96 well plates. PHA (Wellcome Diagnostics, NC) was added to each well at a final concentration of 250 ng/ml. 100 ul of each prediluted test sample was added in triplicate wells. Serial dilutions of recombinant human IL-1β (Genzyme Corp. Boston, Mass.) was used (as controls) to generate standard curves. 96 well plates were incubated for 48–72 hours at 37° C. , 5% $CO_2$. Plates were pulsed with 20uCi/ml $^3$H-Thymidine (Amersham, Arlington, Ill.) and incubated for 6 hours. Cells were harvested with automated cell harvester (Tomtec Harvestor 96, Orange, Conn.) and $^3$H incorporation measured (wallac 1205 Betaplates, Craithersburg, Md.).

H. Immunoprecipitations

Transfected COS cells (3–4×10$^6$ cells/plate) were washed with methionine-free (Meth-) DMEM media and 3 ml of the Meth-DMEM+5% dialysed FCS was added to the plate. Cells were incubated (starved) for 30 minutes at 37° C. , followed by labelling with 200 uCi/ml $^{35}$S methionine (Dupont, Translation grade) for 20 minutes. The cells were washed once with PBS, lysed in 1.3–1.5 ml RIPA buffer (1% NP40, 1% desoxycholate, 0.1% SDS, leupeptin, pepstatin, aprotinin and PMSF) for 30 minutes on ice. Plates were scraped, lysates collected, centrifuged for 15 minutes (14K rpm) at 4° C. (Eppendorf centrifuge) and followed by high speed centrifugation (45K rpm) for 1½ hrs. For pulse-chase experiments cells were pulsed for 20 minutes with 200 uCi/ml $^{35}$S methionine, washed once with PBS and chased by adding culture media (DMEM+10% FCS with arethionine) for defined time intervals.

All lysates were precleared after centrifugation for at least 5 hours with 20 ul of preimmune serum (mixture of 3 bleeds), and then 100 ul of recombinant protein A beads were added for 1 hour (Boehringer Mannheim). Supernatants were collected and 50 ul of additional beads were added for 1 hour at 4° C.

After centrifugation at 14,000 rpm for 5 minutes , 3.0–5.0 ug of affinity purified rabbit-anti-human IL-1β polyclonal IgG was added to each tube of labelled lysate. Cell lysates were incubated with poly sera overnight at 4° C. , and 35 ul of beads were added next morning for 1 hour. The beads were pelleted, washed 8× with lysis buffer and eluted with 25 ul of 2× SDS-PAGE sample buffer, containing 100 mM DTT for 5 minutes at 95° C. . Supernatant was retained dan analysized by SDS-PAGE and visualized by autoradiography.

Example 2

Selection of Stable COS Cell lines Making preIL-1β

COS cells were selected to make preIL-1β expressing stable cell lines. Preliminary studies suggested that COS cells, with and without LPS stimulation, did not release bioactive IL-1β as assessed by D10 bioassays. Transient transfections of genes encoding ICE into COS cells also did not release bioactive mature IL-1β into the supernatant fluid surrounding such cells, suggesting that COS cells do not make preIL-1β or the monkey preIL-1β is not processed by human ICE. Preliminary studies further suggested that transient transfections of human preIL-1β containing plasmids in COS cells did not result in the processing of preIL-1β and the generation of IL-1β bioactivity, suggesting that COS cells lack ICE activity.

COS cells were transfected with the MNC (Neo)-plasmids containing the preIL-1β cDNA construct. Following transfection and selection in G418 for two weeks, 13 clones were randomly picked and expanded. Initially, supernatants from all these clones were collected and tested for bioactivity in D10 or thymocyte proliferation bioassays. No bioactivity was observed in these supernatants. Since preIL-1β is biologically inactive, these results suggested that even if these clones are expressing preIL-1β protein none is being processed and released as bioactive IL-1β. In order to confirm the presence of preIL-1β in these clones, western blot analysis was performed. Seven of 13 clones tested expressed detectable levels of the 31 kDa preIL-1β protein One COS cell clone, termed COS pre 11, was selected and further characterized for the amount of preIL-1β protein made, for the bioactivity in the supernatants and lysates, and for the percent of cells expressing preIL-1β protein in the clonal population.

The half life of preIL-1β protein in COS pre 11 cells was determined. FIG. 3 graphically illustrates that the half life of preIL-1β in COS pre 11 cells is between 2–3 hours . This half life of preIL-1β is consistent with that reported in macrophages/monocytes, in transiently transfected COS cells, and in preIL-1β CHF stable cell lines, These results suggest that stable expression of preIL-1β in COS cells does not adversely affect the stability of the protein.

Example 3

Transfections of Nucleic Acid Encoding ICE, preICE and ICE-like Compositions

The results of Example 2 suggest that the COS pre 11 stable cells express preIL-1↑ protein intracellularly but neither release it into the supernatants nor process it into mature bioactive form. The results suggest that the stability of the preIL-1β protein is not adversely affected in the COS pre 11 cell line. These results also suggest that COS cells do not express ICE.

In this example COS pre 11 cells were transfected with ICE, preICE, and ICE-like compositions to determine if processing of preIL-1β by such compositions would result in the generation of mature bioactive IL-1β in the supernatants, The results are graphically illustrated in FIG. 3. FIG. 3 illustrates the amounts of IL-1β detected by ELISA, in the supernatants of COS pre 11 cells that were transfected with cDNA encoding ICE, preICE and ICE-like compositions. COS pre 11 cells that were transfected with cDNA coding p45, p32, or p20+p10 ICE-like compositions. These results graphically illustrate that mock cells did not produce detectable amounts of IL-1β in the associated supernatant fluid.

Cells transfected with preICE, or ICE-like compositions exhibited a concentration of between 600–800 pg IL-1β/ml in the supernatant. In contrast, no increased IL-1β, over mock, was detected in the supernatants of COS pre 11 cells that were transfected with cDNA encoding for p20 or p10 ICE-like compositions. These cells typically exhibited a concentration of less than 100 pg/ml in the supernatant. Since the ELISA detects both the preIL-1β and mature IL-1β, the results presented in FIG. 3 do not establish if the increased IL-1β in the supernatants was bioactive. Therefore, these supernatants were tested in bioassays.

Figure 4:
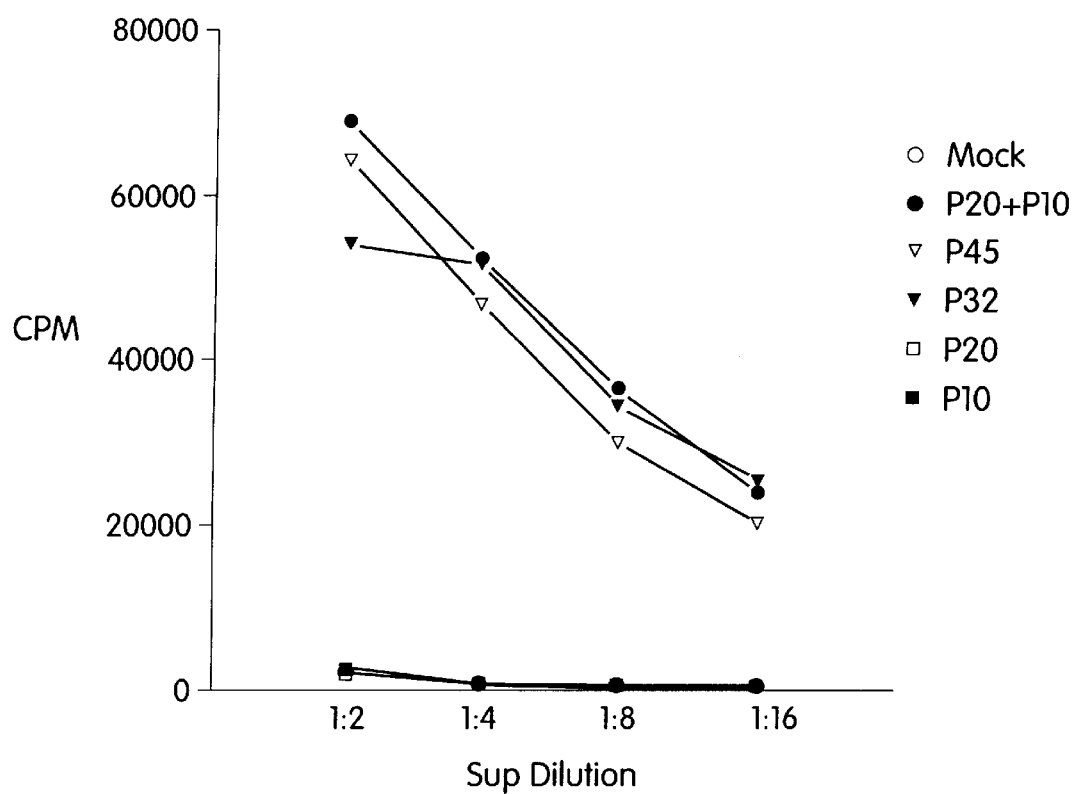
FIG. 4 depicts graphically the production of bioactive, mature IL-1β by cells having a gene for preIL-1β operably linked to a promoter and transiently transfected genes coding ICE, preICE or ICE compositions operably linked to a promoter.

The results of the bioassays are graphically illustrated in FIG. 4. FIG. 4 illustrates the bioactivity of supernatants from COS pre 11 cells transfected with cDNA encoding for ICE, preICE and ICE-like compositions.

As illustrated, data points for mock transfected cells which acted as a control are depicted with open circles. Data points for cells receiving cDNA encoding for both p20 and p10 composition are depicted with closed circles. Data points for cells receiving cDNA encoding for a p45 composition are depicted with a downwardly pointed open triangle. Data points for cells receiving cDNA encoding a p32 composition are depicted with a closed downwardly pointed triangle. Data points for cells receiving cDNA for only a p20 composition are depicted with an open square. Data points for cells receiving cDNA for a p10 composition are depicted with a closed square.

The results suggest that the high levels of IL-1β detected by ELISA in the supernatants of COS pre 11 cells transfected with p45, p32, and p20+p10 correleted with increased bioactivity. In contrast, the supernatants from COS pre 11 cells transfected with p20 or p10 alone did not possess any bioactivity.

These results suggest that the IL-1β, detected in the supernatants of COS pre 11 cells upon transfections of p45, p32, or p20+p10, is processed to bioactive form of IL-1β. However, these results do not address the issue of whether the bioactive material is the 17 kDa mature IL-1 form.

Figure 5:
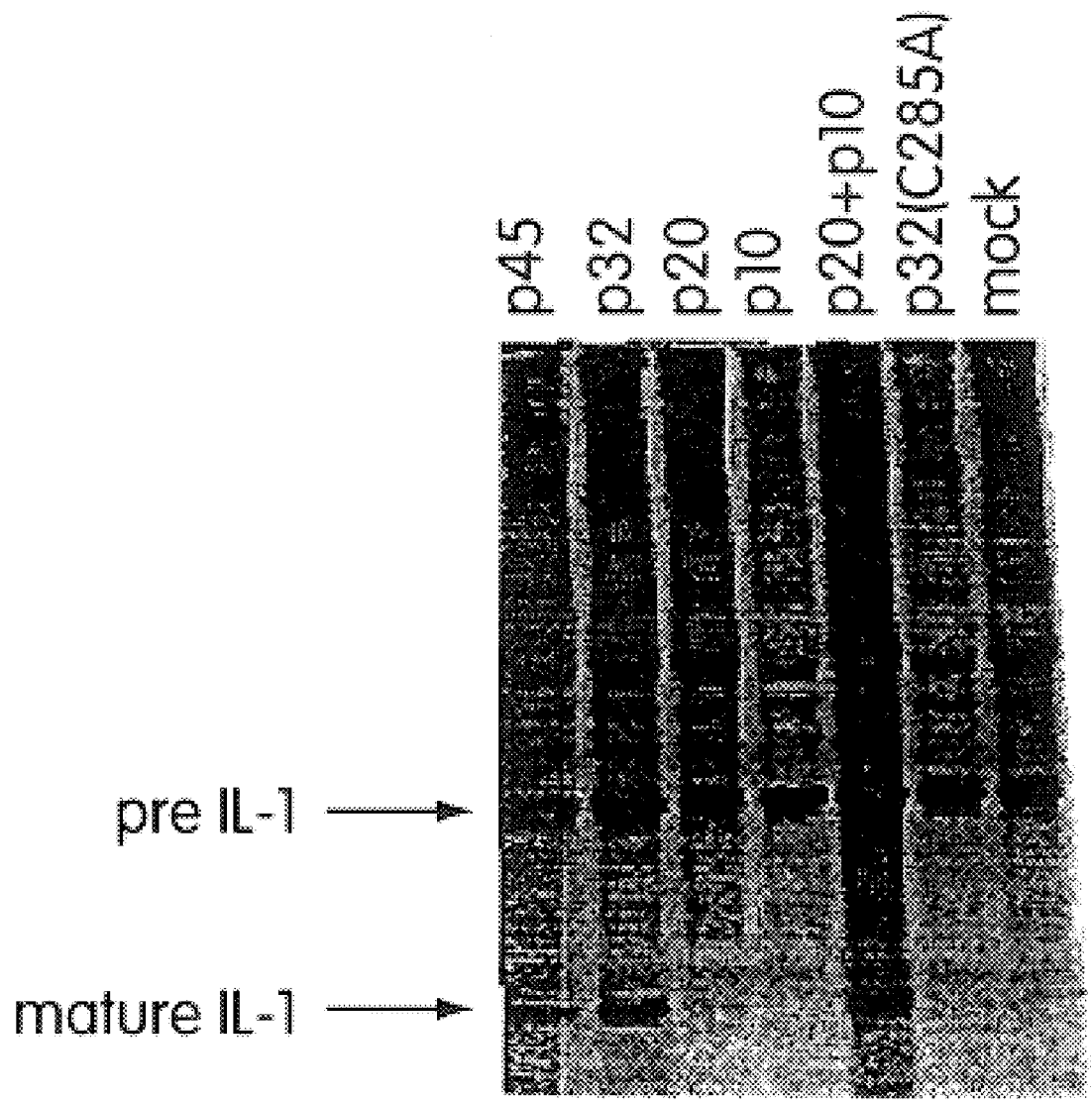
FIG. 5 is a computer scanned copy of a photomicrograph of immunoprecipitation results of IL-1β made by cells transfected with cDNA coding ICE, preICE and ICE-like compositions.

In order to ascertain that the p45, p32, and p20+p10 ICE-like compositions do, indeed, process preIL-1β to its mature bioactive 17 kDa form and that it is this mature form of IL-1 that correlates with bioactivity, immunoprecipitation experiments were performed. FIG. 5 illustrates the results of immunoprecipitation experiments on the lysates and supernatants of COS pre 11 cells transfected with cDNA encoding for ICE-like compositions.

The results depicted in FIG. 5 suggest that both the 31 kDa and the 17 kDa forms of IL-1β are observed in the supernatants of COS pre 11 cells transfected with p45, p32, and p20+p10 ICE-like compositions. In contrast, the 17 kDa form of IL-1β is absent in the supernatants of COS pre 11 cells transfected with either p20 or p10 ICE form alone. Thus, there is a strict correlation between the appearance of 17 kDa IL-1β form and bioactivity of the supernatants.

Example 4

Plasmid Titrations

The results presented above suggest that in a cell the p45, p32, and p20+p10 compositions are capable of processing preIL-1β to a bioactive 17 kDa form of IL-1β and secreting such IL-1β into the environment surrounding the cell. The next series of experiments illustrate the relative preIL-1β processing ability of these ICE-like compositions.

Figure 6:
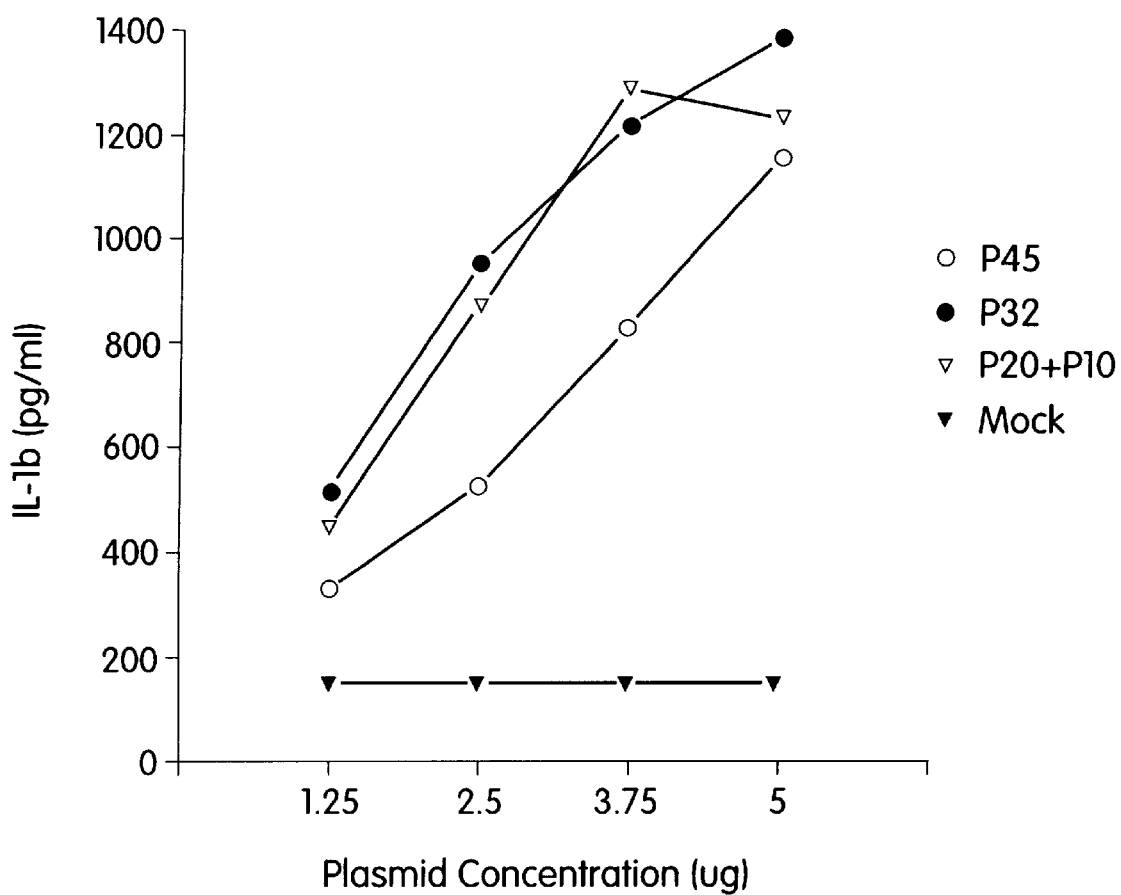
FIG. 6 graphically illustrates the production of IL-1β by cells having a gene for preIL-1β operably linked to a promoter and transiently transfected with ICE, preICE and ICE-like compositions at different plasmid concentrations.

COS pre 11 cells were transfected with 1.25, 2.5, 3.75 and 5 ug of plasmids containing cDNA encoding for ICE and ICE-like compositions. The production of IL-1β was thereafter measured. The results are depicted in FIG. 6. With respect to cells receiving plasmids for both p20 and p10 compositions, an equal amount of each plasmid was first combined and mixed and then transfected. For example, 1.25 ug of p20 and 1.25 ug of p10 were mixed for the 1.25 ug value.

In FIG. 6, data points for cells receiving plasmids having cDNA encoding for a p45 composition are depicted as open circles. Data points for cells receiving plasmids having cDNA encoding for a p32 composition are depicted as closed circles. Data points for cells receiving plasmids having cDNA coding a p20 and p10 composition are depicted as open downwardly pointed triangle. Mock transfected cells are depicted with a closed downwardly pointed triangle.

The results in FIG. 6 suggest that for the same amount of plasmid transfected, a greater amount of IL-1β was detected in the supernatants of COS pre 11 cells transfected with plasmids carrying a cDNA encoding for p32, and cells transfected with two plasmids, one carrying a cDNA encoding for p20 and one carrying a cDNA encoding for p10 (p20+p10) than compared to the amount of IL-1β detected in the supernatants of COS pre 11 cells transfected with a p45 cDNA containing plasmid.

Although p20+p10 and the p32 transfected COS pre 11 cells generated the same amount of IL-1β in the supernatants, the actual efficiency of p20+p10 to process preIL-1β appears to be greater. The p20 and p10 composition requires two plasmids present in the same cell to form the putative active ICE heterodimer. In contrast, with the p32 ICE-like composition, a single plasmid per cell is sufficient for processing preIL-1β. To produce the same amount of IL-1β as p32 transfected cells, cells with the p20 and p10 composition must process preIL-1β more efficiently because there are probably fewer cells with the appropriate plasmid combination. The results in FIG. 6 would suggest that the relative preIL-1β processing ability of the ICE-like compositions is the p20+p10 composition is greater than the p32 composition which is greater than the p45 composition.

Example 5

Specificity Of PreIL-1β Processing

This Example demonstrates the ICE-like compositions p45, p32, and p20+p10, processing preIL-1β and generating bioactive 17 kDa IL-1 in the supernatant, by processing preIL-1β at the ICE cleavage site (Asp 116-Ala 117). Plasmids having cDNA encoding for p45, p32, and p20+p10 compositions were co-transfected into COS cells with either preIL-1β or a preIL-1β mutant. In the preIL-1β mutant, the ICE cleavage site Asp 116-Ala 117 was mutated to Asn 116-Val 117. This preIL-1β mutant was not cleaved by THP.1 lysates in an in vitro ICE cleavage assay. The same preIL-1β mutant was cleaved by chymotrypsin which cleaves preIL-1β, three amino acid residues upstream of the ICE cleavage site. Furthermore, pulse-chase experiments suggest that this preIL-1β mutant composition is expressed as efficiently as the correct preIL-1β composition and that the half-lives of both proteins are the same, approximately 2–3 hours in COS cells.

Figure 7:
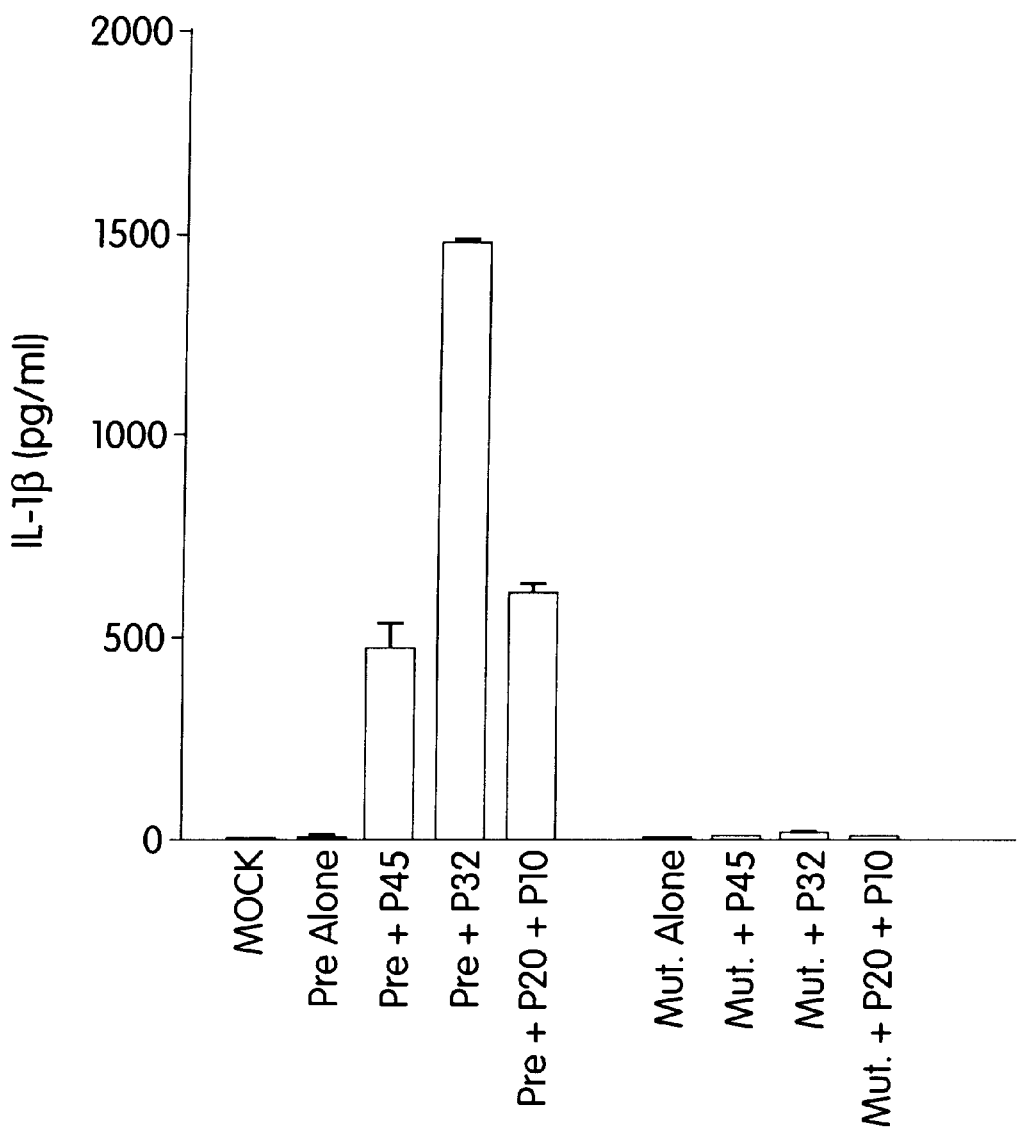
FIG. 7 depicts in bar graph form the production of IL-1β (as determined by ELISA) by COS-1 cells co-transfected with genes for preIL-1β or genes for a mutant preIL-1β and genes coding ICE, preICE and ICE-like compositions.

The results of the processing of preIL-1β and preIL-1β mutant are illustrated graphically in FIG. 7. The data of FIG. 7 suggest that cotransfection of COS cells with cDNA encoding for preIL-1β and either p45, p32 or p20+p10 ICE-like compositions resulted in an increased appearance of IL-1β in the supernatant. In contrast, cotransfection of COS cells with cDNA encoding for a preIL-1β mutant and either p45, p32, or p20+p10 ICE-like composition did not result in an increased appearance of IL-1β in the supernatant.

Figure 8:
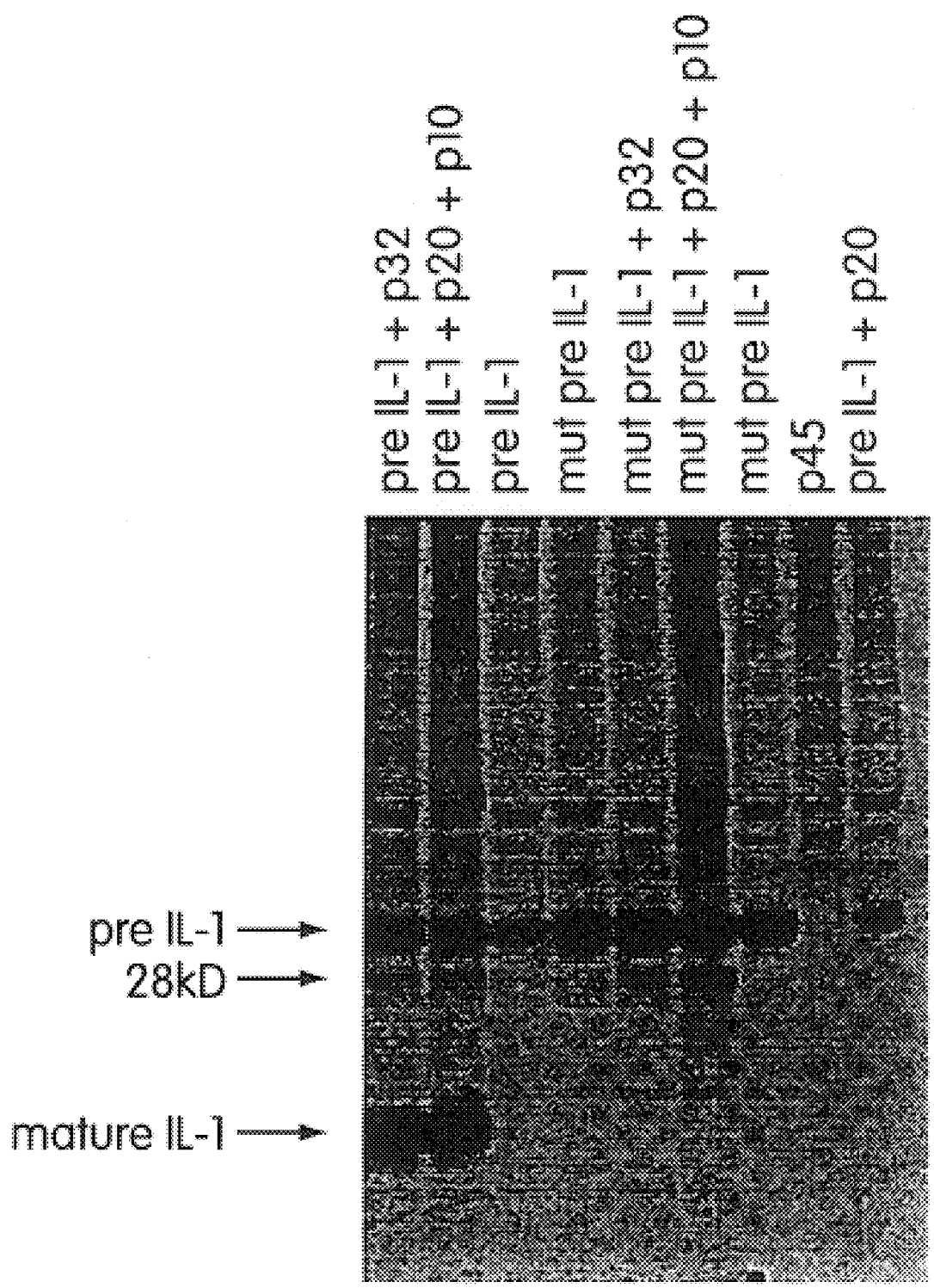
FIG. 8 is a computer scanned copy of an autoradiograph depicting immuno-precipitation of IL-1β of cells transfected with preIL-1β and various ICE-like compositions.

Immunoprecipitation experiments suggest that increased IL-1β release from preIL-1β+p45, preIL-1β+p32, and preIL-1β+p20+p10 cotransfected COS cells correlated with the appearance of an immunoprecipitatable 17 kDa band of IL-1β in the supernatant. These results are graphically illustrated in FIG. 8. The lack of appearance of IL-1β (FIG. 7) from COS cells cotransfected with cDNA coding preIL-1β mutant and ICE or ICE-like compositions also correlated with the lack of appearance of the 17 kDa immunoprecipitatable band in the supernatant.

Some COS cells cotransfected with cDNA encoding for preIL-1β mutant and an ICE-like composition, exhibited an immunoprecipitatable 28 kDa band in the lysates. This band represents the first ICE cleavage site in the preIL-1β molecule between positions Asp 27-Gly28. This cleavage site was not mutated in the preIL-1β mutant. Collectively, the results presented in FIG. 8 suggest that the p45, p32, and p20+p10 ICE-like compositions process preIL-1β at the correct ICE cleavage site in vivo.

Example 6

Transfection to Produce PreIL-1β and ICE Double Stable and ICE Single Stable COS Cell Clones This Example describes the transfection of COS cells to produce preIL-1β and ICE double stable and ICE single stable COS cell clones. COS cells were either cotransfected with preIL-1β and p45 ICE, preIL-1β and p32 ICE, or either p45 ICE or p32 ICE containing MNC vectors. This vector also contains a neomycin resistance gene. COS cell clones incorporating preIL-1β and p20 and p10 ICE-like compositions would be made in a similar manner. G418 resistant clones were selected three weeks after transfection. The positive double stable clones (sometime abbreviated herein as D.S.) expressing both the preIL-1β and p45 ICE or preIL-1β and p32 ICE, were selected by their ability to constitutively release mature bioactive IL-1β into the supernatants. The amounts of mature bioactive IL-1β released from the individual clones were determined by ELISA and/or bioassay. The positive single stable COS cell clones (sometimes referred herein as S.S.) expressing p45 ICE or p32 ICE were selected by their ability to release mature bioactive IL-1β into the supernatants following transfections of preIL-1β cDNA containing plasmids Example 7

Selection of Double Stable (preIL-1β+ICE) and Single Stable (ICE alone) COS Cell Clones This Example describes the criteria for the selection of double stable (preIL-1β+ICE) and single stable (ICE alone) COS cell clones. The numbers of double stable and single stable clones picked, expanded, and analysed. Double stable (preIL-1β+ICE) COS cell clones were analyzed for the constitutive release of mature IL-1β into the supernatant. Single stable (ICE) COS cell clones were analyzed for the ability of ICE (p45 or p32) to process preIL-1β and release mature IL-1β into the supernatants. These results are depicted in Table 7.

TABLE 7

Selections of Double and Single Stable COS Cell Clones

|  | # Clones tested for IL-1β release | # of + ve Clones | IL-1β release (range; pg/ml) |
| --- | --- | --- | --- |
| Double Stables |  |  |  |
| preIL-1β + p45 ICE | 74 | 41 | 20–500 |
| preIL-1β + p32 ICE | 58 | 11 | 2–14 |
| Single Stables |  |  |  |
| p45 ICE | 11 | 7 | * |
| p32 ICE | 11 | 5 | * |

*Details presented in Table 8

The results presented in Table 7 suggest that, in the case of preIL-1β+p45 ICE double stable COS cell clones, 41 out of 74 clones analysed were positive for the constitutive release of IL-1β into the supernatants. The amount of IL-1β detected in the supernatants of individual clones varied between 20–500 pg/ml/5×10$^5$ cells after 48 hrs of culture at 37° C. However, in the case of preIL-1β and p32 ICE double stable COS cell clones only 11 out of 58 clones analyzed were positive for the constitutive release of mature IL-1β. Moreover, in this case, the amounts of IL-1β detected in the supernatants of positive clones varied between 2 and 14 pg/ml/5×10$^5$ cells after 48 hrs of culture, at 37° C. Table 7 also shows the numbers of p45 ICE and p32 ICE single stable COS cell clones picked, expanded and analysed. These ICE single stable COS cell clones were transfected with preIL-1β containing plasmids and the amounts of mature IL-1β released into the supernatants was determined.

Seven p45 ICE single stable COS cell clones and five p32 ICE single stable COS cell clones were transfected with preIL-1β containing plasmids and 48 hrs later supernatants were collected. The amount of mature IL-1β present in the supernatants was determined by ELISA. COS cells were also transfected with mature IL-1β cDNA containing plasmids. These mature IL-1β cDNA transfected COS cells were used as positive controls. Supernatants from such cells were collected 48 hrs after transfection. The amounts of mature IL-1β present in the supernatants were determined by ELISA. Mock cells were COS cells transfected with plasmids containing no cDNA inserts and used as negative controls. The amounts of mature IL-1β present in the supernatants were determined by ELISA.

Table 8 sets forth the amounts of mature IL-1β detected in the supernatants of individual p45 ICE and p32 ICE single stable COS cell clones.

TABLE 8

Selections of ICE Single Stable
COS Cell Clones
Mature IL-1β detected in supernatants (ng/ml)

| Clone # | p45 ICE Clones | Clone # | p32 ICE Clone |
|---|---|---|---|
| 1 | 2.68 | 1 | 5.38 |
| 2 | 4.32 | 2 | 5.23 |
| 3 | 2.39 | 3 | 3.0 |
| 4 | 1.76 | 4 | 0.48 |
| 5 | 5.54 | 5 | 5.32 |
| 6 | 6.28 | | |
| 7 | 6.28 | | |
| Mature IL-1β | 6.28 | | 5.68 |
| Mock | 0.00 | | 0.00 |

Example 8

Characterization of Double Stable (preIL-1β and p45 ICE) Clones as High, Intermediate, and Low IL-1β Producers This Example describes features of selected double stable clones with respect to IL-1β production. Of the 41 perIL-1β and p45 ICE double stable COS cell clones, nine clones were expanded for further characterization. Based on the amounts of mature IL-1β released into the supernatants of these clones, after 48 hrs of culture at 37° C., the clones were classified as high producers (>300 pg/ml 5×10$^5$ cells), intermediate producers (between 100–300 pg/ml/5×10$^5$ cells), and low producers (<100 pg/Ml/5×10$^5$ cells). Similary, five preIL-1β and p32 ICE double stable COS cell clones were expanded for further analysis. These clones released between 2–14 pg/ml mature IL-1β/5×10$^5$ cells. The characterization of clones as high, intermediate and low producers is useful for applications involving screening, the relationship with apoptosis and antiapoptosis mechanisms and the relationship with temperature sensitive mechanisms.

The characterization of clones expressing preIL-1β and p45 ICE is set forth in Table 9 below:

TABLE 9

Characterization of Double Stable
COS Cell Clones

| Clone # | Characterization of Clones* | IL-1β detected in supernatant (pg/ml)** |
|---|---|---|
| preIL-1β + p45 ICE | | |
| 2 | HP | 500 |
| 10 | HP | 400 |
| 58 | HP | 365 |
| 34 | IP | 113 |
| 36 | IP | 143 |
| 63 | IP | 124 |
| 50 | LP | 13 |
| 66 | LP | 41 |
| 70 | LP | 20 |
| preIL-1β + p32 ICE | | |
| 32 | LP | 5 |
| 34 | LP | 2 |
| 50 | LP | 3 |

TABLE 9-continued

Characterization of Double Stable
COS Cell Clones

| Clone # | Characterization of Clones* | IL-1β detected in supernatant (pg/ml)** |
|---|---|---|
| 51 | LP | 2 |
| 52 | LP | 14 |

*HP, hiqh producer; IP, intermediate producer; LP, low producer
**pg/ml IL-1β/5 × 10$^5$ cells plated. Supernatants were collected after 48 hours of culture at 37° C. and the amounts of IL-1β determined by ELISA.

Example 9

Figure 9:
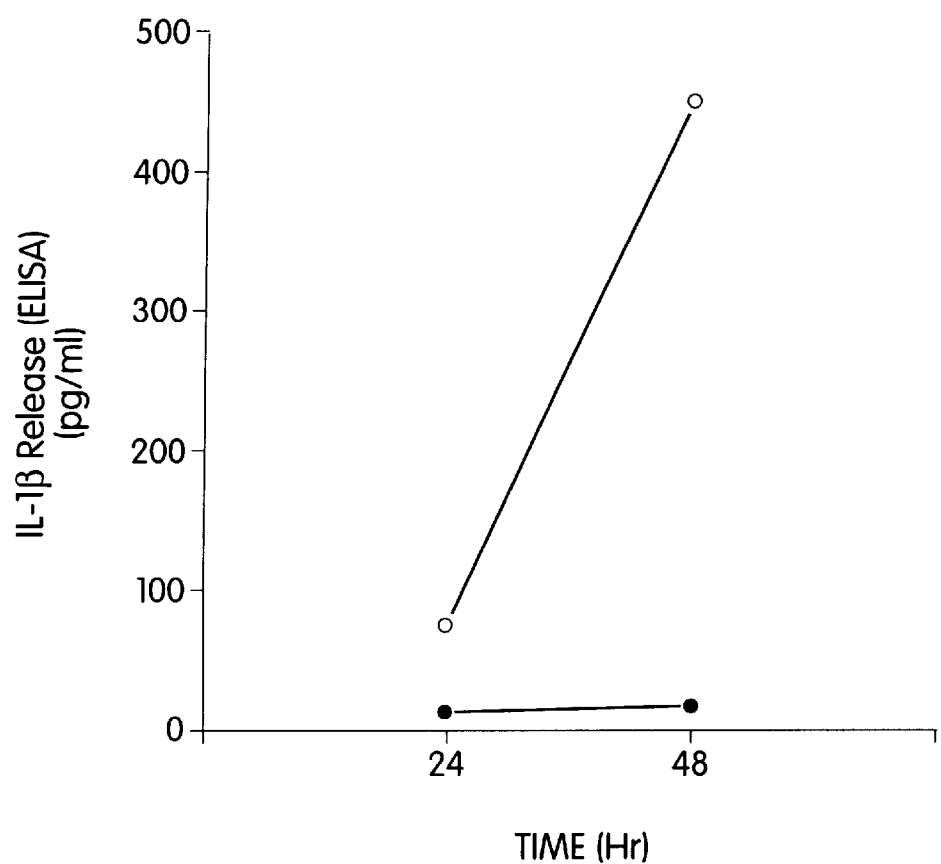
FIG. 9 graphically depicts IL-1β release from double stable COS cell clones #58 and 70 which clones stably express preICE and preIL-1β.

Kinetics and bioactivity of IL-1β Released into the Supernatants of Double Stable Clones Two double stable clones, #58 (high producer) and #70 (low producer), were cultured to determine the kinetics of mature IL-1β release. 5×10$^5$ cells were plated/well in a 6 well plate at 37° C. Supernatants were collected at 24 hrs and 48 hrs. The amount of mature IL-1β in the supernatants was determined by ELISA. The results are depicted graphically in FIG. 9. Clone #58 is represented by points comprising open circles. Clone #70 is represented by points comprising solid circles. The results show that clone #58 cells constitutively release IL-1β into the supernatants. However, no constitutive release of mature IL-1β into the supernatants was observed from clone #70 cells over time. These results were surprising and unexpected in that clone #70 had previously been identified as a low producer of IL-1β.

Figure 10:
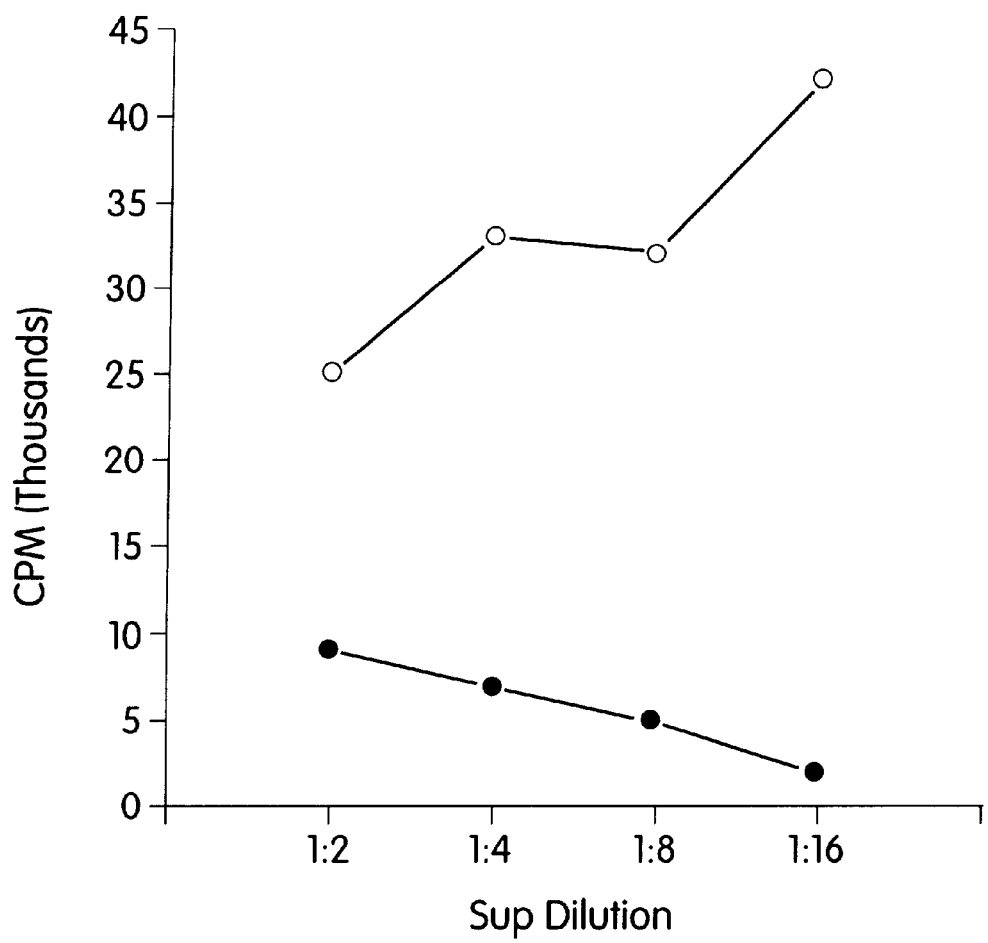
FIG. 10 graphically depicts IL-1β bioactivity in supernatants derived from double stable COS cell clones #58 and 70 which clones stably express preICE and preIL-1β.

The supernatants collected at 48 hrs from clones #58 and #70 were tested in the D10 proliferation assay to determine if the released IL-1β is bioactive. The results are depicted graphically in FIG. 10. Clone #58 is represented by points comprising open circles and clone #70 is represented by points comprising solid circles. The results show that the supernatants derived from clone #58 possess bioactive IL-1β. The results confirm that the supernatants of clone #70 did not comprise mature IL-1β. In previous studies an extremely close correlation between the values obtained by IL-1β ELISA and bioassays was observed.

Example 10

Loss of IL-1β Release From Double Stable COS Cell Clones

The results set forth in this Example suggest that preIL-1β and p45 ICE expressing cells could be made and such cells were capable of constitutively releasing mature, bioactive IL-1β. However, surprisingly and unexpectedly, these same cells exhibited a decline in their ability to produce and release mature bioactive IL-1β over time.

Double stable COS cell clones were cultured at 37° C. over prolonged periods of time to study the stability of IL-1β production and release. It was observed that the constitutive production and release of mature IL-1β into the supernatant declined to almost undetectable levels. All double stable clones tested (>20 clones) for constitutive IL-1β release showed a similar gradual loss of IL-1β release. However, the loss of IL-1β release from different clones occurred at different times. With some clones the loss of IL-1β release was observed within a month. For other clones it took up to 3–5 months of culture.

COS cell clones were selected in G418 for 3 weeks and then expanded. The cells were grown at 37° C. over several passages. At 4, 16, 20, 24, and 26 weeks, for clones #58 and #2, 5×10$^5$ cells/well were plated for 48 hours. The supernatants were collected and levels of IL-1β determined by ELISA. Both the double stable clones #58 and #2 were characterized as high producers (for details see Table 9).

PreIL-1β and mature IL-1β single stable COS cell clones were grown at 37° C. over several passages. At 16 and 20 weeks, for preIL-1β constructs and at 8 and 20 weeks for mature IL-1β constructs, 5×10$^5$ cells/well were plated for 48 hours. The supernatants were collected and levels of IL-1β determined by ELISA.

p45 ICE and p32 ICE single stable COS cell clones were grown at 37° C. over several passages. At 6 and 16 weeks, these cells were transfected with preIL-1β cDNA containing plasmids and the amounts of IL-1β released into the supernatants were determined by ELISA. These data are summarized in Table 10 below:

TABLE 10

Kinetics of Loss of IL-1β Release from Double Stable COS Cell Clones

| Clone # | Duration of culture at 37° C. (Wks) | IL-1β Detected supernatants (pg/ml) |
|---|---|---|
| Double Stables | | |
| preIL-1β+ p45 ICE | | |
| #58 | 4 | 300 |
|  | 16 | 46 |
|  | 20 | 68 |
|  | 24 | 9 |
|  | 26 | 8 |
| #2 | 4 | 400 |
|  | 16 | 21 |
|  | 20 | 29 |
|  | 24 | 6 |
|  | 26 | 5 |
| Single Stables | | |
| preIL-1β | 16 | 10 |
|  | 20 | 12 |
| Mature IL-1β | 8 | 5,000 |
|  | 20 | 4,172 |
| p45 ICE | 6 | 2,100 |
|  | 16 | 2,600 |
| p32 ICE | 6 | 1,746 |
|  | 16 | 1,836 |

In contrast to the decline in mature IL-1β production are release from double stable COS cell clones, a similar decline in the ablity of ICE (p45 and p32) single stable COS cell clones to process and release mature IL-1β was not observed. Similarly, when mature IL-1β cDNA was stably expressed in COS cells no significant decline in constitutive mature IL-1β production and release was observed from these clones.

These results suggest that ICE plays an important role in the release of mature bioactive IL-1β from cells. These results also suggest that the prodomain of preIL-1β plays an important role in the ICE-mediated release of mat IL-1β. Southern Blot analysis suggests that the decrease in the release of mature IL-1β from double stable COS cell clones is not due to loss of inserts (preIL-1β/ICE). Northern and PCR analysis suggest that the decrease is not due to lack of transcription (preIL-1β/ICE). Immunoprecipitations suggest that the decrease is not due to lack of protein (preIL-1β/ICE).

These results suggest that COS cells express an antiapoptosis gene which counteracts the apoptotic effect of ICE. These results are surprising and unexpected in that one might expect cell lines to diminish the expression of a gene for an apoptosis composition such as ICE over time. Single stable ICE producing COS cells have utility to identify compositions and genes which inter act with the apoptotic mechanisms of the cell.

Example 11

Restoration of Mature IL-1β Release From Double Stable COS Cell Clones

The results suggest that the decline in constitutive mature IL-1β release from the double stable COS cell lines was not due to the loss of inserts, loss of transcription, or the loss of protein. This Example describes features of the COS cell clones related to the decline and methods for restoring IL-1β release from these cells.

Figure 11:
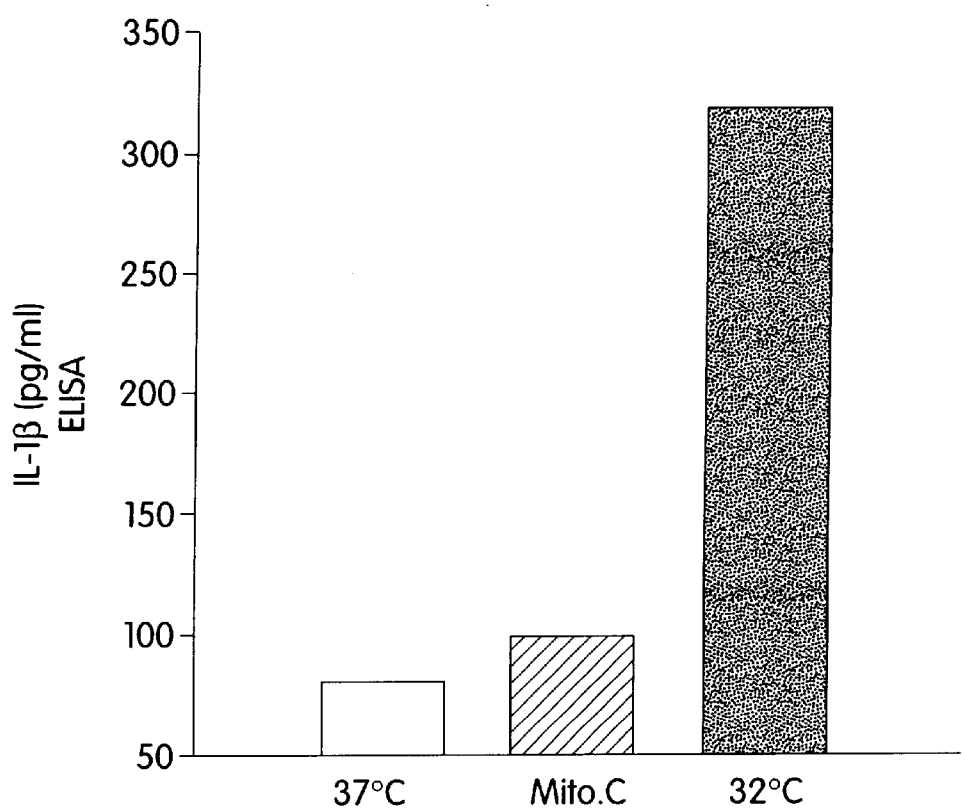
FIG. 11 graphically depicts the effects of 37° C. temperatures, 32° C. temperatures and mitomycin C on IL-1β release from double stable COS cell clone #58 which clone stably expresses preICE and preIL-1β.

One potential parameter which may contribute to the loss was the rate of proliferation of COS cells. COS cells have a doubling time of about 8–10 hrs. Thus, initial experiments were designed to determine if prolonging the doubling time would result in increased production and release of IL-1β from double stable COS cells. In an attempt to prolong the doubling time of double stable COS cells, such cells were cultured under various conditions. Double stable clone #58 cells were either treated with mitomycin C or cultured at 32° C. Mitomycin C prevents cells from dividing and proliferating. The amount of IL-1β released over a 48 hour time period is graphically presented in FIG. 11. The results suggest that clone #58 cells cultured at 37° C. produce and release a low amount of IL-1β in the supernatants. Clone #58 cells treated with mitomycin C produced and released approximately the same amount of IL-1β. However, when clone #58 cells were cultured at 32° C. , a dramatic increase in IL-1β release into the supernatants was observed. Culturing clone #58 cells at 32° C. , also prolonged the doubling time of these cells such that at least 4-fold less cells were recovered after 48 hrs of culture at 32° C. as compared to the numbers of cells recovered after 48 hrs of culture at 37° C.

The increase in IL-1β production in view of the smaller cell population is surprising and unexpected. Further, although expressing an apoptosis composition, such as ICE or an ICE-like composition, such cells did not exhibit apoptosis.

Figure 12:
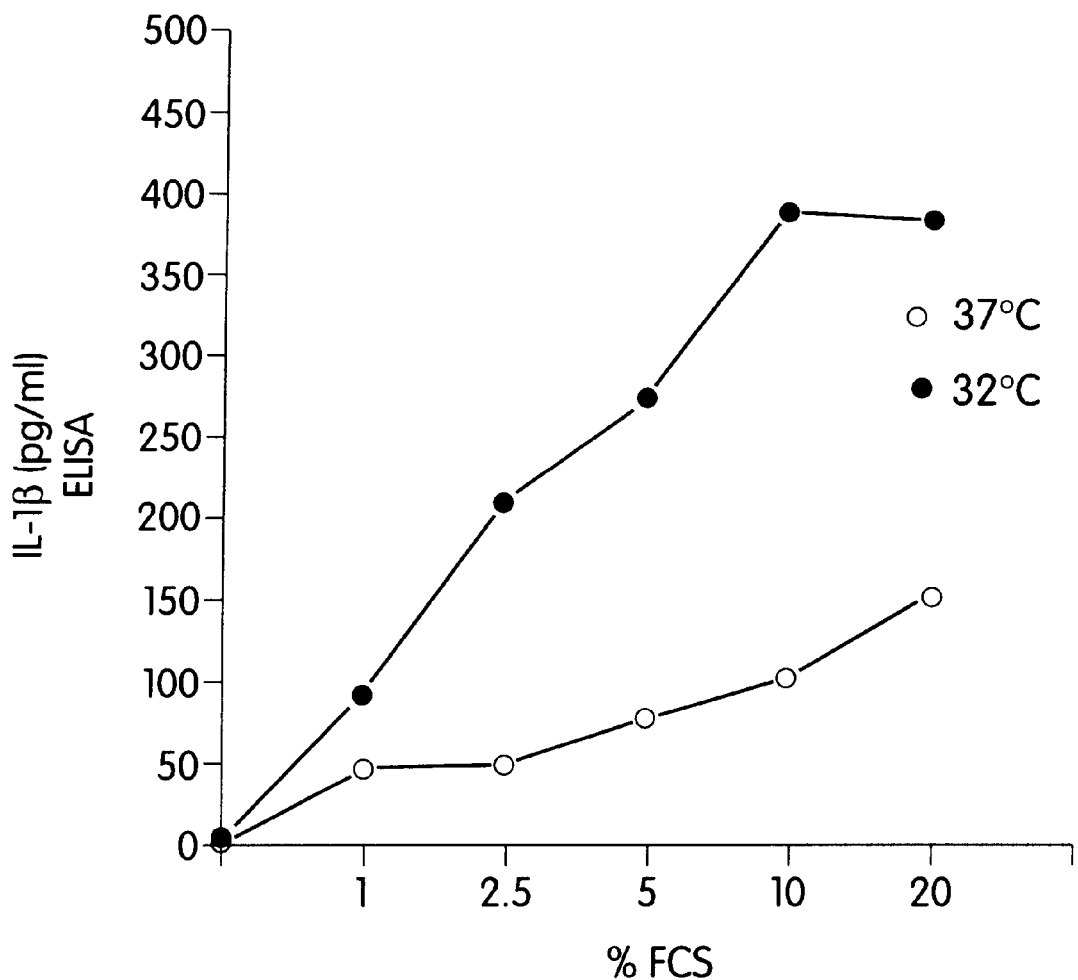
FIG. 12 graphically depicts the effect of FCS concentrations on IL-1β release from double stable COS cell clone #58 which clone stably expresses preICE and preIL-1β.

Culturing COS cells in media containing low concentrations of fetal calf serum (FCS) also prolongs the doubling time of COS cells. Thus, an experiment was designed to determine if reducing FCS concentrations in the culture media would also result in an increase in IL-1β release. Clone #58 D.S. cells were cultured in decreasing concentrations of FCS at either 37° C. or 32° C. and IL-1β release was measured in the supernatants. These results are depicted graphically in FIG. 12. The results suggest that at 37° C. , IL-1β release from clone #58 cells increases with the increase in FCS concentration i.e. low FCS concentrations that prolong the doubling time do not result in increased IL-1β release. In contrast, at all FCS concentrations tested, significantly greater amounts of IL-1β were released into the supernatants of clone #58 cells cultured at 320C. These results collectively suggest that low temperature, rather than prolonged doubling time per se, might be crucial for the restoration of IL-1β release from double stable COS cells.

It has also been observed that double stable COS cell clones that express greater amounts of ICE loose their ability to constitutively release IL-1β faster than the clones that express less ICE. The greater amounts of ICE may induce a temperature sensitive mechanism that might interfere with preIL-1β and ICE interaction.

PreIL-1β and p32 ICE double stable COS cell clones that initially released only 2–14 pg/ml of IL-1β (Tables 9 & 10) showed a dramatic increase in IL-1β release (up to 500 pg/ml) when cultured at 32° C. In order for these double stable clones to start releasing high amounts of IL-1β they had to be cultured at 32° C. for more than 4 days (as opposed to the preIL-1β and p45 ICE double stable clones that showed increased IL-1β release within 24–48 hrs). It should be pointed out that the p32 form of ICE is much more active than the p45 form of ICE as determined by plasmid titration experiments. (See: FIG. 6).

It is plausible that the decline in the constitutive release of mature IL-1β from double stable cells over time may be due to activation of a temperature sensitive mechanism(s) that somehow either prevents the preIL-1β/ICE interaction and/or interferes with IL-1β release. These temperature sensitive mechanisms may be related to the presence of viral or endogenous mammalian homologs of serpins.

Figure 13A:
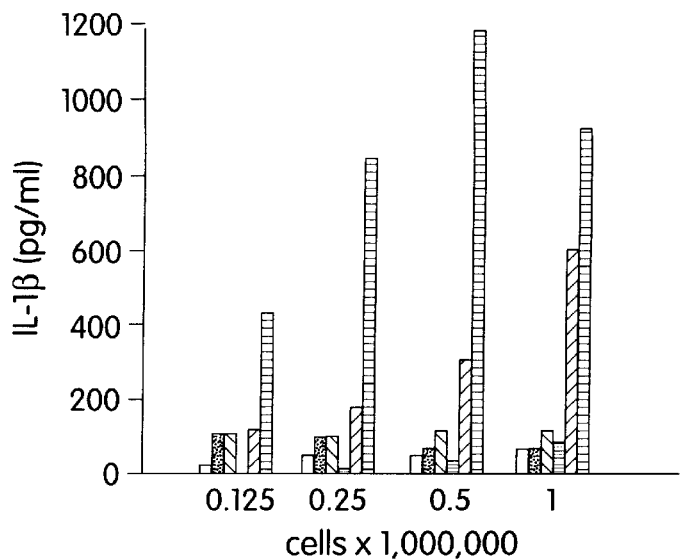
FIGS. 13a, 13b and 13c depict in bar graph form the release of IL-1β from three double-stable COS cell clones maintained at different temperatures.
Figure 13B:
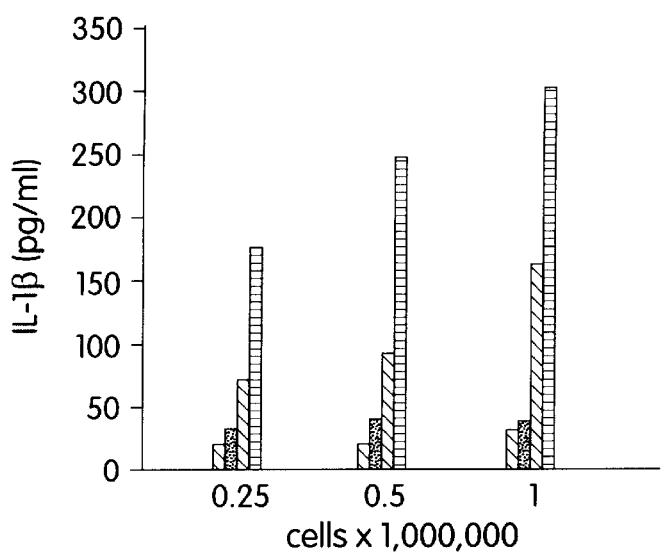
Figure 13C:
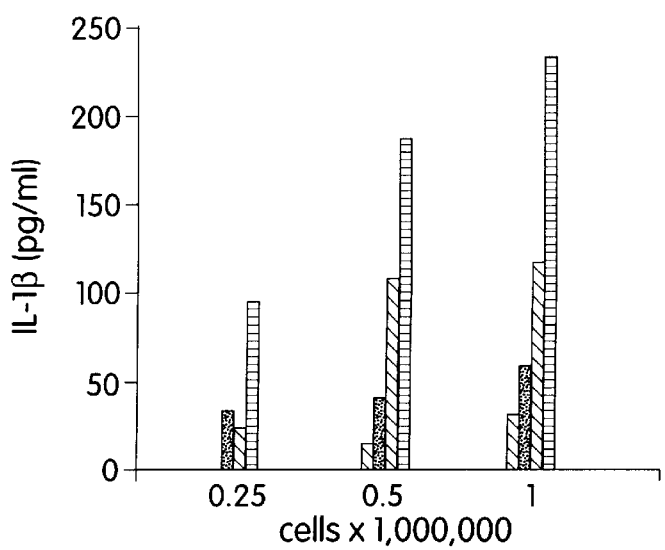

The results presented in FIG. 13 show that the restoration of IL-1β release at 32° C. can be achieved with several double stable COS cell clones. Restoration of IL-1β release was observed with all double stable COS cells clones tested. Two groups of clone #58 cells, two groups of clone #36 cells and two groups of clone #2 cells were evaluated at various times. Each group of clone #58 cells was evaluated at 24, 48 and 72 hours. Each group of clones #36 and clone #2 was evaluated at 48 and 72 hours. One group of each clone was maintained at 37° C. and a second group of each clone was maintained at 32° C. IL-1β production and release is graphically depicted in bar graph form in FIG. 13a, with respect to clone #58, FIG. 13b with respect to clone #36, and FIG. 13c with respect to clone #2. In FIG. 13a, the group maintained at 37° is represented by heavy lines drawn diagonally from bottom right up to top left at 24 hours, a solid bar at 48 hours and by light lines drawn diagonally, from bottom right up to top left at 72 hours. The group maintained at 32° C. is represented by light cross-hatched vertical and horizontal lines at 24 hours, light lines drawn diagonally from bottom left to top right at 48 hours, and by light cross-hatched diagonal lines at 72 hours.

The results with respect to groups of clone #36 cells and clone #2 cells are depicted in FIGS. 13b and 13c respectively. The group maintained at 37° C. at 48 hours is represented by heavy diagonal lines drawn from lower right extending to upper left, and at 72 hours by a solid bar. The group maintained at 32° C. at 48 hours is represented by light diagonal lines drawn from lower right to upper right and at 72 hours by cross-hatched lines.

Based on the above information it appears that both the rapidity with which the loss of IL-1β release from double stable clones is observed and the period of time required (at 32° C.) to restore IL-1β release from these double stable clones might depend upon the level of expression of ICE and/or ICE activity in double stable COS cells.

Example 12

Restoration of IL-1β Release from Double Stable COS Cells—Effect of Temperature

Figure 14:
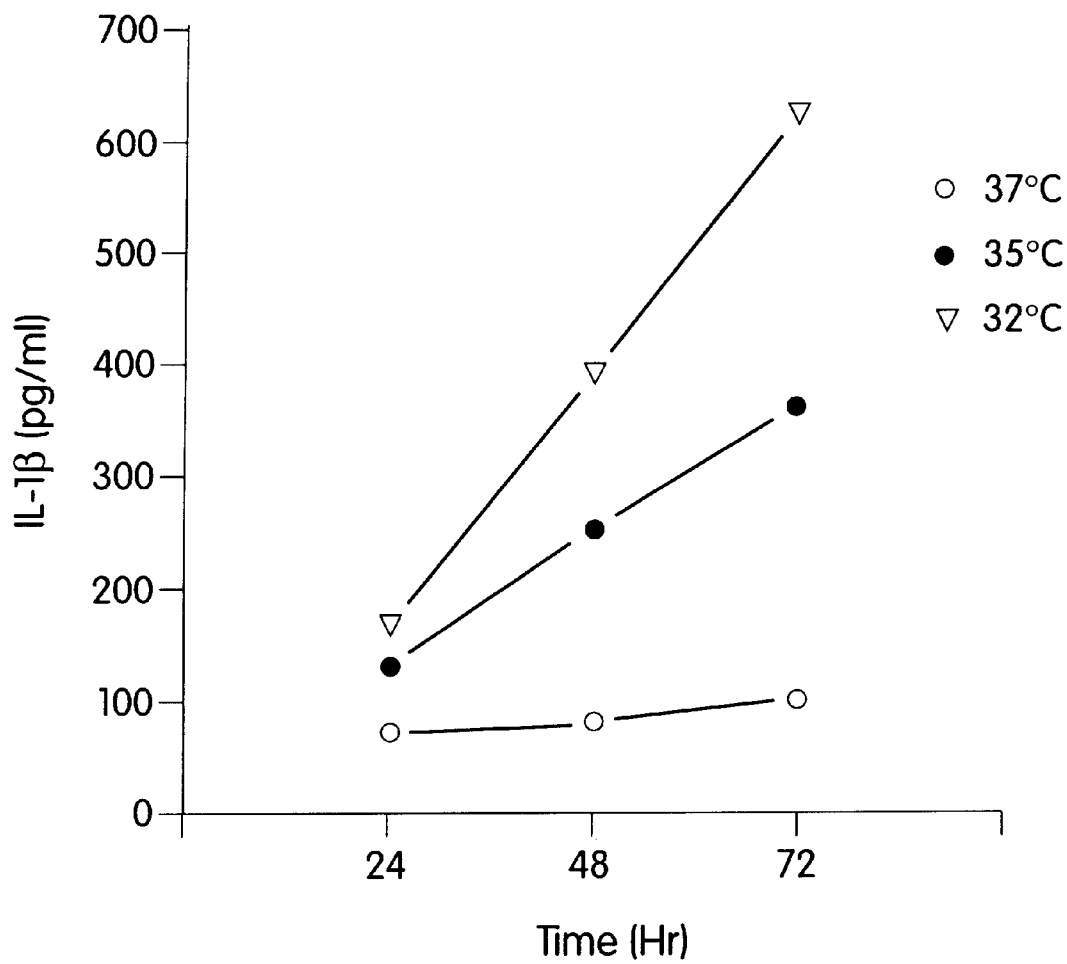
FIG. 14 depicts the kinetics of IL-1β release from double-stable COS cell clone #58 cultures at different temperatures.

This Example describes the effect of low temperatures on IL-1β release. Double stable clone #58 cells were cultured in 6-well plates, at either 37° C., 35° C. or 32° C. for 24, 48, and 72 hours, and the amounts of IL-1β released into the supernatants, over time, was determined by ELISA. The results are depicted in FIG. 14, where open circles represent cells maintained at 37° C., solid circles represent cells maintained at 35° C. and downwardly pointed open triangles represent cells at 32° C.

The results suggest that greater amounts of IL-1β are released into the supernatants as the temperature decreases. These results suggest that the mechanism(s) that interfere(s) with either preIL-1β/ICE interaction and/or IL-1β release is (are) extremely temperature sensitive.

Example 13

Significance of the Prodomain of Pre IL-1β in ICE-mediated Processing and Release of IL-1β

IL-1β does not possess a classical signal peptide and, therefore, is not secreted via the classical secretory pathway. The single and double stable COS cell clones of the present example suggest an IL-1β release mechanism(s) and a role of the prodomain of preIL-1β.

Equal cell numbers of several preIL-1β and ICE double stable COS cell clones, matIL-1β and ICE double stable COS cell clones, and matIL-1β single stable COS cell clones were cultured and the amounts of IL-1β were determined in the cell lysates and supernatants. The percent of total IL-1β released into the supernatants was determined for each of the above clones. The results from these experiments are summarized in FIG. 15. No IL-1β was released into the supernatants from the prerIL-1β single stable COS cell clones. In comparison, 50–60% of total IL-1β made was released into the supernatants from preIL-1β and ICE double stable COS cell clones, these results suggest that the processing of preIL-1β by ICE and the release of matIL-1β are linked events. Only 1–10% of the total IL-1β made is released into the supernatants from matIL-1β single stable and matIL-1β and ICE double stable COS cell clones. These results suggest that in the absence of the prodomain of IL-1β, ICE is not involved in the release of matIL-1β from cells. Collectively, the results summarized in FIG. 15 show that ICE plays an important role in the release of IL-1β from cells only when the prodomain of IL-1β is present. Therefore, the prodomain of preIL-1β interacts with ICE, at a site distinct from the active site of ICE. Inhibitors of this second interaction between the prodomain of preIL-1β and the non-active site of ICE block or inhibit the release of IL-1β from cells.

Example 14

Optimization of the Double Stable COS Cell Based Screening Assay for ICE-inhibitors Double stable COS cells are useful for screening for chemicals which alter the preIL-1β processing and release pathway. A preferred double stable clone is clone #58. However, the preference for clone #58 is based on selection criteria which can be readily applied to other clones as well. Preferably, the cells are grown at a temperature between 27° and 37° C. and, more preferably temperatures between 29° and 33° C., and most preferably, 31° and 33° C. Preferably, compounds are applied to the cultured cells which are maintained at a temperature of between 32 d and 37° C. and, more preferably, 32° to 35° C. for a period of 24–72 hours, and most preferably about at least 48 hours. These conditions may be maintained longer and the ranges presented are preferred ranges which provide consistent results. These conditions allow detection of mature IL-1β by ELISA.

Results obtained with a double stable COS cell such as clone #58 cells can be examined against a counterscreen double stable COS cell clone. The counterscreen cell stably expresses genes for mature IL-1β and p45 ICE. However, the counterscreen cell clone does not process IL-1β or release IL-1β through the action of ICE. A preferred counterscreen cell is clone #10 which cell is deposited with the ATCC under the designation of Accession No. CRL 11694.

The compounds that come up positive as ICE inhibitors in double stable clone #58 cells (i.e. inhibit the processing of preIL-1β and/or release of mature IL-1β) are tested in the counterscreen. In the counterscreen these positive compounds should not inhibit the release of IL-1β.

Example 15

Double Stable COS Cell-Based Screen and Counters,reen for ICE Inhibitors

This Example features the use of a positive screen cell and a counterscreen cell to identify inhibitors of ICE. Double stable clone #58 (positive-screen) and clone #10 (counterscreen) cells were grown at 37° C. in T75 flasks. At the start of the experiment, $3 \times 10^4$ cells/well were plated in a 96-well flat bottom plate, with and without the Ac-YVAD-CHO peptide inhibitor of ICE at 35° C. After 48 hrs of incubation, supernatants were harvested and analys ed for IL-1β release by ELISA.

Figure 16A:
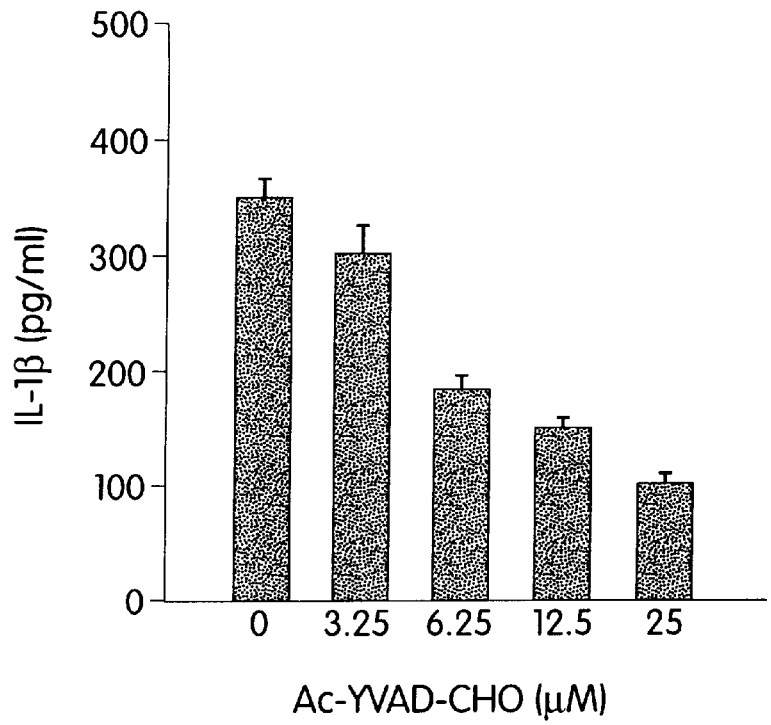
FIGS. 16a and 16b depict in bar graphs the release pattern of a positive screen cell and a counter-screen cell under the influence of an inhibitory peptide Ac-YVAD-CHO, which inhibits ICE activity.
Figure 16B:
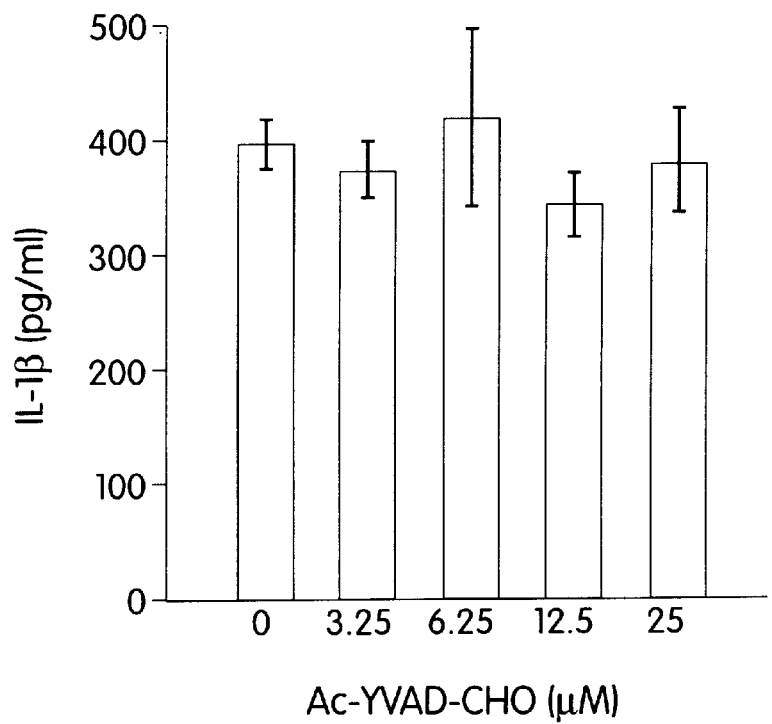

The results are presented in bar graph form in FIG. 16. Data derived from positive screen cells is depicted in solid bar form and data derived from counter-screen cells is depicted by cross-hatching. These results suggest that a dose dependent inhibition of IL-1β release is observed from double stable clone #58 in the presence of Ac-YVAD-CHO, whereas, no inhibition of IL-1β release is observed from the counterscreen clone, clone #10, in the presence of the same ICE inhibitor.

These results collectively suggest that the cell based screen and the counterscreen that have been developed respond as expected to identify ICE inhibitors, inhibitors of the preIL-1β and ICE interaction, or inhibitors of IL-1β release, and would also respond as expected to identify ICE agonists, agonists of the preIL-1β and ICE interaction, or agonists of IL-1β release. And, these results suggest that the cell based screen would respond as expected to compounds that interact with the prodomain of preIL-1β or features of ICE which interact with the prodornain of preIL-1β, as agonists or inhibitors of such reactions.

Example 16

Mutation of the putative active site cysteine

This example suggests that the putative active site cysteine 285 contributes to the enzyme activity of ICE in vivo. ICE-like compositions were mutated to alter the cysteine 285 residue to alanine or serine in the p32 ICE form and to alanine in the p20 ICE form. Any observed inactivity of the p32 form could be directly correlated to the active site rather than the inability to undergo processing to generate a p20+ p10 heterodimer, if the p20 form of the cys 285 mutant was also inactive. In these experiments the p20 with the cys 285 mutation (p20-mut) was cotransfected with the wild type p10 containing plasmid.

Figure 17:
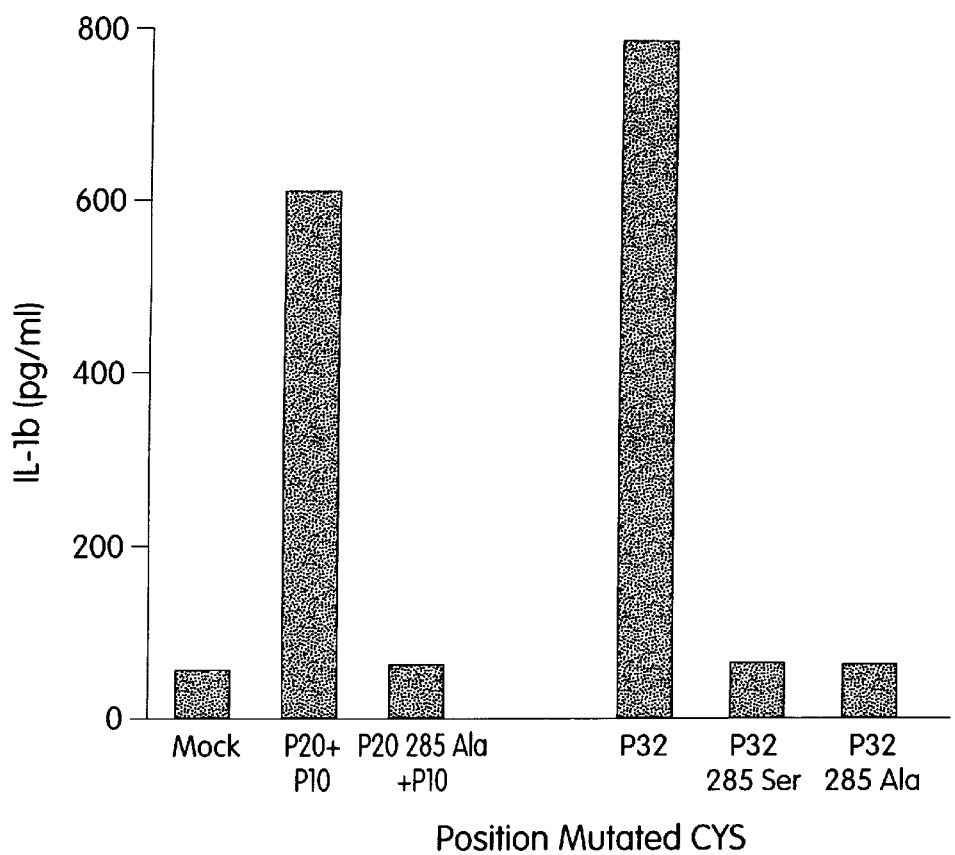
FIG. 17 graphically depicts the production of IL-1β by COS-preII cells transiently transfected with preiL-1β genes and ICE-like compositions with substitutions at selected amino acid positions.

The ability of these constructs to process preIL-1β is graphically illustrated in FIG. 17. The results suggest that this mutation of the putative active site cysteine in both the p32 and p20 ICE-like composition completely abolishes the appearance of IL-1β in the supernatants of COS pre 11 cells. Neither biroctivity, nor the 17 kDa IL-1β form could be observed in these supernatants. These results suggest that the cysteine 285 residue plays an important functional role. These examples further illustrate the use of cells and methods of the present invention in identifying compositions and nucleic acids coding for such compositions which have ICE-like activity.

Example 17

Identification of ICE Inhibitors

This example highlights the use of cells made in accordance with the present invention for use in identifying ICE inhibitors. Cells cotransfected with genes for the ICE-like compositions, p32, p45 and p10+p20, and a further gene for preIL-1β, each operably linked to a promoter, would be evaluated for their sensitivity to inhibitory substances.

These inhibitory substances have been described in PCT/US91/06595 as having the formula:

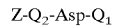

where Z is an end terminal blocking group; $Q_2$ is 0 to about 4 amino acids such that the sequence $Q_2$-Asp corresponds to at least a portion of the sequence Ala-Tyr-Val-His-Asp, amino acids 112–116 of preIL-1β;and $Q_1$ is an electronegative leaving group.

The functional group Z is described as a C1–C6 alkyl, benzyl, acetyl, C1–C6 alkoxycarbonyl, benzyloxycarbonyl or C1–C6 alkyl carbonyl. Alkyl refers to linear or branch chains having 1–6 carbon atoms, which may be optionally substituted. Representative alkyl groups are described as methyl, ethyl, propyl, isopropyl, butyl, pentyl, hexyl and the like. In a more preferred embodiment, Z is described as t-butyl, butoxyl carbonyl, t-butoxycarbonyl, acetyl or benzyloxycarbonyl.

$Q_2$ is described as preferably comprising one amino acid, preferably His, Phe, Pro, or Tyr. Most preferably, $Q_2$ is His or Phe.

$Q_1$ is described as an aldehyde, diazoalkyl keytone or haloalkyl keytone. Electronegative leaving groups are described as chemical groups susceptible to nucleophilic attack. Alkyl refers to linear or branched chain radicals having 1–3 carbon atoms, which may be optionally substituted. Representative alkyl groups include methyl, ethyl, propyl and the like.

$Q_1$ is described as preferably an aldehyde or fluoromethyl keytone.

It is reported that these compounds are or can be synthesized by methods known in the art. See PCT/US91/06595.

The present invention affords a simple method in which each of the groups Z, $Qt_2$, and $Q_1$ can be evaluated for the action in inhibiting the formation of IL-1β. Cells having a gene for preIL-1β operably linked to a promoter and also having a gene for ICE, preICE or an ICE-like composition operably linked to a promoter would be placed in conditions in which preIL-1β and ICE, preICE or ICE-like compositions are formed which in turn allow the cell to make IL-1β.

European patent application 92305670.9 describes ICE inhibitory compositions as having the formula:

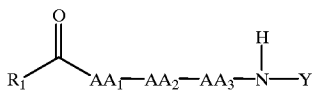

or a pharmaceutically acceptable salt thereof: wherein Y is:

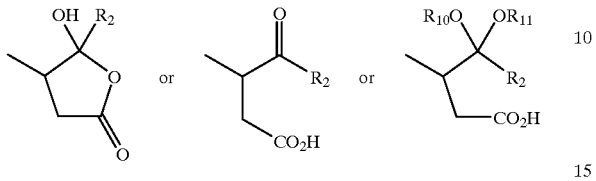

As reported, $R_1$ is
(a) substituted $C_{1-12}$ alkyl, wherein the substituent is selected from
hydroxy,
halo, and
$C_{1-6}$ alkylcarbonyl;
(b) aryl $C_{1-6}$ alkyl wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazinyl,
(17) indolyl,
(18) purinyl,
(19) isoxazolyl, and
(20) oxazolyl,
and mono and di-substituted aryl as defined above in items (1) to (20) wherein the substituents are independently $C_{1-6}$ alkyl, halo, hydroxy, $C_{1-6}$ alkyl amino, $C_{1-6}$ alkoxy, $C_{1-6}$ alkyithio, and $C_{1-6}$ alkylcarbonyl;
$R_2$ is
(a) H,
(b) deuterium, (c)

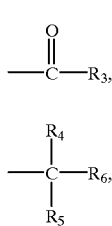

wherein $R_3$ is
(1) substituted $C_{1-6}$ alkyl, wherein the substituent is selected from
(a) hydrogen,
(b) hydroxy,
(c) halo, and
(d) $C_{1-6}$ alkyl carbonyl,
(2) aryl $C_{1-6}$ alkyl or substituted aryl $C_{1-6}$ alkyl as defined above, wherein the aryl may be mono and di-substituted the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

(d)
$$-\overset{O}{\underset{\|}{C}}-R_3,$$

(e)
$$-\overset{R_4}{\underset{R_5}{C}}-R_6,$$

wherein $R_4$ and $R_5$ are each individually selected from hydrogen, fluorine and hydroxy;
$R_6$ is selected from the group consisting of
(1) hydrogen,
(2) fluorine,
(3) substituted $C_{1-6}$ alkyl wherein the substituent is selected from
(a) hydrogen,
(b) hydroxy,
(c) halo,
(d) $C_{1-6}$ alkylcarbonyl,
(4) aryl $C_{1-6}$ alkyl,
wherein the alkyl is substituted with hydrogen, oxo, $C_{1-3}$ alkyl, halo or hydroxy,
wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;
(5) $C_{1-6}$ alkyl amino carbonyl $C_{1-6}$ alkyl or $C_{1-6}$ alkyl carbonyl amino $C_{1-6}$ alkyl,
(6) aryl amino carbonyl $C_{1-6}$ alkyl or aryl carbonyl amino $C_{1-6}$ alkyl,
wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;
(7) aryl $C_{1-6}$ alkyl amino carbonyl $C_{1-6}$ alkyl or aryl $C_{1-6}$ alkyl carbonyl amino $C_{1-6}$ alkyl,
wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;
$R_{10}$ and $R_{11}$ are each independently
(a) hydrogen,
(b) $C_{1-6}$ alkyl,
(c) aryl $C_{1-6}$ alkyl, wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,

(12) quinolyl,
(13) isoquinolyl,
(14) benzofuryl,
(15) benzothienyl,
(16) pyrazinyl,
(17) indolyl,
(18) purinyl,
(19) isoxazolyl, and
(20) oxazolyl, and mono and di-substituted aryl as defined above in items (1) to (20) wherein the substituents are independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl, or $R_{10}$ and $R_{11}$ are joined together to form a ring of 5 to 7 carbon atoms, said ring having 2 heteroatoms;

$AA_1$ is independently selected from the group consisting of
(a) a single bond, and
(b) an amino acid of formula AI

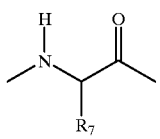

wherein $R_7$ is selected from the group consisting of:
(a) hydrogen,
(b) substituted $C_{18}$ alkyl, wherein the substituent is selected from
   (1) hydrogen,
   (2) hydroxy,
   (3) halo,
   (4) —S—$C_{1-4}$ alkyl
   (5) —SH
   (6) $C_{1-6}$ alkylcarbonyl,
   (7) carboxy, (8)

(9) amino carbonyl amino,
   (10) $C_{1-4}$ alkylamino, wherein the alkyl moeity is substituted with hydrogen or hydroxy, and the amino is substituted with hydrogen or CBZ,
   (11) guanidino, and
(c) aryl $C_{1-6}$ alkyl,
   wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkexy, $C_{1-6}$ alkylthio, and $C_{1-6}$ alkylcar bonyl, $AA_2$ is independently selected from the group consisting of
(a) a single bond, and (b) an amino acid of formula AII

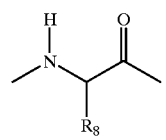

$AA_3$ which are each independently selected from the group consisting of
(a) a single bond, and
(b) an amino acid of formula AIII

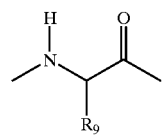

wherein $R_8$ and $R_9$ are each independently selected from the group consisting of
(a) hydrogen,
(b) substituted $C_{1-6}$ alkyl, wherein the substituent is selected from
   (1) hydrogen,
   (2) hydroxy,
   (3) halo,
   (4) —S—$C_{1-4}$ alkyl
   (5) —SH
   (6) $C_{1-6}$ alkylcarbonyl,
   (7) carboxy, (8)

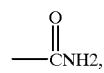

(9) amino carbonyl amino,
   (10) $C_{1-4}$ alkylamino, wherein the alkyl moiety is substituted with hydrogen or hydroxy, and the amino is substituted with hydrogen or CBZ,
   (11) guanidino, and
(c) aryl $C_{1-6}$ alkyl,
   wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl.

One class of this genus is the compounds wherein:
$R_1$ is
(a) substituted $C_{1-6}$ alkyl, wherein the substituent is selected from
   (1) hydrogen,
   (2) hydroxy,
   (3) chloro or fluoro, and
(b) aryl $C_{1-6}$ alkyl wherein the aryl group is selected from the group consisting of
   (1) phenyl,
   (2) naphthyl,
   (3) pyridyl,
   (4) furyl,
   (5) thienyl,
   (6) thiazolyl,
   (7) isothiazolyl,
   (8) benzofuryl, (9) benzothienyl,
(10) indolyl,
(11) isooxazolyl, and
(12) oxazolyl, and mono and di-substituted $C_{6-10}$ aryl as defined above in items (1) to (12) wherein the substituents are independently $C_{1-4}$ alkyl, halo, and hydroxy;

$R_2$ is
(a) H,
(b) deuterium,

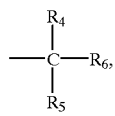
(c)

wherein $R_4$ and $R_5$ are each individually selected from hydrogen, fluorine and hydroxy;
$R_6$ is selected from the group consisting of
(1) hydrogen,
(2) fluorine,
(3) substituted $C_{1-6}$ alkyl wherein the substituent is selected from
  (a) hydrogen,
  (b) hydroxy,
  (c) halo,
  (d) $C_{1-6}$ alkylcarbonyl,
(4) aryl $C_{1-6}$ alkyl,
  wherein the alkyl is substituted with hydrogen, oxo, $C_{1-3}$ alkyl, halo or hydroxy,
  wherein aryl is defined as immediately above, and
  wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;
(5) $C_{1-6}$ alkyl amino carbonyl $C_{1-6}$ alkyl or $C_{1-6}$ alkyl carbonyl amino $C_{1-6}$ alkyl,
(6) aryl amino carbonyl $C_{1-6}$ alkyl or aryl carbonyl amino $C_{1-6}$ alkyl,
  wherein aryl is defined as immediately above, and
  wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;
(7) aryl $C_{1-6}$ alkyl amino carbonyl $C_{1-6}$ alkyl or aryl $C_{1-6}$ alkyl carbonyl amino $C_{1-6}$ alkyl,
  wherein aryl is defined as immediately above, and
  wherein the aryl may be mono and di-substituted, the substituents being each independently C1-6 alkyl, halo, hydroxy, $C_{1-6}$ alkyl amino, $C_{1-6}$ alkoxy, $C_{1-6}$ alkylthio, and C1-6 alkylcarbonyl;

$R_{10}$ and $R_{11}$ are each independently hydrogen or $C_{1-3}$ alkyl;

$AA_1$ is independently selected from the group consisting of
(a) a single bond, and
(b) an amino acid of formula AI

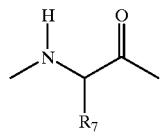

wherein $R_7$ is aryl $C_{1-6}$ alkyl
  wherein aryl is defined as immediately above, and
  wherein the aryl may be mono and di-substituted, the substituents being each independently $C_{1-6}$ alkyl, halo, hydroxy, $C_{1-6}$ alkyl amino, $C_{1-6}$ alkylthio, and $C_{1-6}$ alkycarbonyl;

$AA_2$ is independently selected from the group consisting of
(a) a single bond, and
(b) an amino acid of formula AII

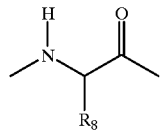

$AA_3$, which are each independently selected from the group consisting of
(a) a single bond, and
(b) an amino acid of formula AIII

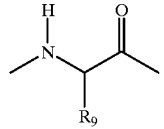

wherein $R_8$ and $R_9$ are each independently selected from the group consisting of
(a) hydrogen,
(b) $C_{1-6}$ alkyl, wherein the substituent is selected from
  (1) hydrogen,
  (2) hydroxy,
  (3) halo,
  (4) —S—$C_{1-4}$ alkyl
  (5) —SH
  (6) $C_{1-6}$ alkylcarbonyl,
  (7) carboxy,

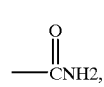
(8)

(9) $C_{1-4}$ alkylamino, and $C_{1-4}$ alkyl amino wherein the alkyl meity is substituted with an hydroxy, and
(10) guanidino, and
(c) aryl $C_{1-6}$ alkyl,
  wherein aryl is defined as immediately above, and
  wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl.

Within this class are the compounds wherein $AA_1$, $AA_2$ and $AA_3$, are each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

Alternatively, within this class are the subclass of compounds wherein $R_1$ is $C_{1-3}$ alkyl;

$R_2$ is hydrogen, deuterium or

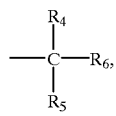

and $R_8$ and $R_9$ are each individually
 (a) hydrogen,
 (b) $C_{1-6}$ alkyl,
 (c) mercapto $C_{1-6}$ alkyl,
 (d) hydroxy $C_{1-6}$
 (e) carboxy $C_{1-6}$ alkyl,
 (f) aminocarbonyl $C_{1-6}$ alkyl,
 (g) mono— or di-$C_{1-6}$ alkyl amino $C_{1-6}$ alkyl,
 (h) guanidino $C_{1-6}$ alkyl,
 (i) amino-$C_{1-6}$ alkyl or N-substituted amino-$C_{1-6}$ alkyl wherein the substituent is carbobenzoxy,
 (j) carbamyl $C_{1-6}$ alkyl, or
 (k) aryl $C_{1-6}$ alkyl, wherein the aryl group is selected from phenyl and indolyl, and the aryl group may be substituted with hydroxy, $C_{1-3}$ alkyl.

Within this sub-class are the compounds wherein:

$R_1$ is methyl;

$R_2$ is hydrogen;

$R_8$ is $C_{1-6}$ alkyl; and $R_9$ is
 (a) hydrogen,
 (b) $C_{1-6}$ alkyl,
 (c) benzyl,
 (d) p-hydroxy-benzyl,
 (e) N-carbobenzoxy-amino-(n-butyl),
 (f) carbamylmethyl,
 (g) carbamylethyl,
 (h) indol-2-yl-methyl,
 (i) substituted phenyl $C_{1-6}$ alkyl, wherein the substituent is hydrogen, hydroxy, carboxy, or $C_{1-4}$ alkyl,
 (j) substituted indolyl $C_{1-6}$ alkyl, wherein the substituenr is hydrogen, hydroxy, carboxy, or $C_{1-4}$ alkyl, or
 (k) substituted imidazolyl $C_{1-6}$ alkyl wherein the substituent is hydrogen, hydroxy, carboxy, or $C_{1-4}$ alkyl.

Exemplifying the invention are the following compounds:
 (a) N-(N-Acetyl-tyrosinyl-valinyl-lysinyl)-3-amino-4-oxobutanoic acid;
 (b) N-(N-Acetyl-tyrosinyl-valinyl-g-CBZ-lysinyl)-3-amino-4-oxobutanoic acid;
 (c) N-(N-Acetyl-tyrosinyl-valinyl-lysinyl)-3-amino-4-oxobutanoic acid; or a ring chain tautomer or hydrate thereof.

The following equilibrium form of Y

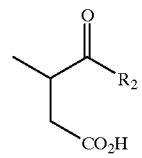

are intended to include the following equilibrium forms as well:

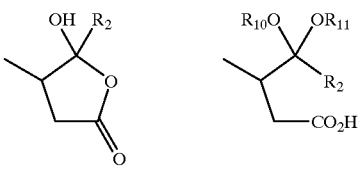

These compositions are reported as being made or as capable of being made by conventional methods of synthesis.

Compositions which are capable of interacting with the prodomain of IL-1β or the regions of ICE that interact with the prodomain and, thus, interfere with preIL-1β processing by ICE are evaluated in a similar manner. Compositions which are capable of interacting with apotosis compositions, such as ICE, preICE, and ICE-like compositions, and anti-apototic compositions, such as Bcl-2, Bcl-x p35 and ced-9 are evaluated in a similar manner.

A substance to be evaluated is applied to the cell in a manner in which the cell receives or is interacted with the substance. Typically, the cell is challenged with differing concentrations of the substances, ranging from 0.01–1 M/ml. The cell is monitored to assess IL-1β production in the supernatant or in lysates of the cells. A reduction or complete absence of IL-1β over controls is indicative of an inhibitory composition. An elevation of IL-1β production over controls is indicative of an agonist composition.

These examples describe the establishment and characterization of preIL-1β stable COS cell line (COS pre 11 cell line) as well as several single and double stable COS cell clones. The data on COS pre 11 cells suggest that these cells neither process preIL-1β nor release it into the supernatants, and that these cells lack preIL-1β processing activity and/or secretion machinery.

However, transient expression of either p45 corresponding to preICE or a p32 ICE-like composition or the components of the active ICE heterodimer together (but not the individual components) into these COS pre 11 cells resulted in the processing of preIL-1β and the appearance of the 17 kDa mature bioactive IL-1β form into the supernatants. PreIL-1β processing mediated by ICE is demonstrated by results showing that all forms of active ICE do not process preIL-1β mutant in which the ICE cleavage site has been altered. Moreover, mutation of the putative active site cysteine abolishes the preIL-1β processing ability of ICE.

These examples also describe results of cotransfections to produce double and single stable COS cell clones. The results of these studies are consistent with the COS pre 11 results. The data further suggest that the rate of IL-1β release is diminished over time in the double stable clones. It appears from the data that both the loss of release of IL-1β and the time period required to restore the IL-1β release may depend on the level of expression of ICE and/or ICE activity in these cells.

The double stable COS cells have been used in the aforementioned examples in a cell-based screening assay and counterscreen for ICE inhibitors. This assay provides an accurate and much needed mechanism for screening ICE inhibitors. The data suggests ICE is necessary for processing preIL-1β to mature IL-1β and that the prodomain may play a role in the release of IL-1β from the cell.

The method and cells of the present application are reproducible and quantitative. These features allow an assessment of the relative preIL-1β processing ability of the ICE and ICE-like compositions. The results suggested in the examples demonstrate that transfections with cDNA coding p32 or p20+p10 together generated more IL-1β in the supernatants of COS pre 11 cells than the transfection with cDNA for p45. Those results suggest that p32 and p20+p10 compositions are more active than p45 compositions.

Surprisingly and unexpectedly these data suggest that the p20+p10 composition is more active than p32, since the probability of two plasmids entering the same cell is less than the probability of a single functional plasmid entering a COS pre 11 cell. Assuming that the transfection efficiency of both the p20 and the p10 plasmids entering the same number of COS pre 11 cells is less than the efficiency of a single p32 plasmid, it would appear that the separately processed and combined p20+p10 composition is more active in processing preIL-1β than the p32 composition. Surprising and unexpectedly, the relative preIL-1β processing ability of the various ICE forms in a COS cell clone screening assay of the separately expressed p20+p10 composition is greater than the p32, which in turn is greater than the p45, which corresponds to precursor ICE. In contrast, other workers have suggested that the relative preIL-1β processing ability of the various ICE forms of p45 is greater than the p32 composition, which is greater than the p20 composition, which is greater than the p10 composition.

One of the surprising and unexpected observations is the complete reconstitution of the two components (p20+p10). These two separately expressed components of ICE come together and are folded by cellular machinery to form the active ICE heterodimer. The active heterodimer formed within a COS cell, in the presence of preIL-1β, retained its specificity for the ICE cleavage site (Asp. 116-Ala 117). The same heterodimer formed by the separately expressed components did not process the preIL-1β mutant that lacks the ICE cleavage site. Similarly, the p45 and the p32 ICE forms did not process the preIL-1β mutant.

The results, suggesting that the separately expressed p20 and p10 components are refolded to form ICE or an ICE-like composition, are surprising and unexpected. Other workers have failed to reconstitute the activity of ICE by cotransfecting p20 and p10 into COS cells. Others have suggested ICE could only be formed from the 45 kDA or 32 kDA preICE molecule.

The present invention features a direct assay for compositions having ICE activity. The present invention further features a practical method of screening compositions for ICE inhibitory activity, ICE agonist activity and IL-1β release inhibitions. The invention further features a method for screening compositions for apoptosis inhibitory or agonist activity.

Thus, this invention has been described and illustrated. It will be apparent to those skilled in the art that many variations and modifications can be made without departing from the purview of the appended claims and without departing from the teaching and the scope of the present invention.

What is claimed is:

1. A method for identifying a composition with activity in Interleukin-1β (IL-1β) processing or secretory pathways comprising:
providing a non-naturally occuring cell that has been modified to comprise a first gene for precursor IL-1β (preIL-β) operably linked to a promoter, and a second gene selected from the group consisting of: (a) a gene for Interleukin-1β Converting Enzyme (ICE), (b) a gene for an ICE-like molecule capable of processing preIL-β to mature IL-β (matIL-β) and (c) a gene for a test composition to be evaluated, the second gene being operably linked to a promoter;
the first and second genes being stably incorporated into the cell;
culturing the cell at a temperature of 29° C. to 35° C., for at least 72 hours and under conditions sufficient for expression of the first and second genes by the cell;
applying to the cell a test composition to be evaluated when the second gene is a gene for ICE or an ICE-like molecule capable of processing preIL-β to matIL-β; and
monitoring the cell or the cell environment for a change in the concentration of preIL-1β or matIL-1β, as compared to the concentration of preILβ or matIL-1β in the absence of the test composition, which change identifies the test composition as a composition having activity in IL-1β processing and secretory pathways.

2. The method of claim 1, wherein the cell is cultured at a temperature of 34° C.

3. The method of claim 1, wherein the cell is cultured at a temperature of 35° C.

4. A method for identifying a composition with activity in Interleukin-1β (IL-1β) processing or secretory pathways comprising:
providing a non-naturally occurring cell that has been modified to comprise a first gene for precursor IL-1β (preIL-β) operably linked to a promoter, and a second gene selected from the group consisting of: (a) a gene for Interleukin-1β Converting Enzyme (ICE), (b) a gene for an ICE-like molecule capable of processing preIL-β to mature IL-β (matIL-β) and (c) a gene for a test composition to be evaluated, the second gene being operably linked to a promoter;
The first and second genes being stably incorporated into the cell;
culturing the cell at a temperature of 29° C. to 33° C., under conditions and for a period of time sufficient for expression of the first and second genes by the cell;
applying to the cell a test composition to be evaluated when the second gene is a gene for ICE or an ICE-like molecule capable of processing preIL-β to matIL-β; and
monitoring the cell or the cell environment for a change in the concentration of preIL-1β or matIL-1β, as compared to the concentration of preILβ or matIL-1β in the absence of the test composition, which change identifies the test composition as a composition having activity in IL-1β processing and secretory pathways.

5. The method of claim 4, wherein the cell is cultured at a temperature of 29° C.

6. The method of claim 4, wherein the cell is cultured at a temperature of 30° C.

7. A method for identifying a composition with activity in Interleukin-1β (IL-1β) processing or secretory pathways comprising:

providing a non-naturally occurring cell that has been modified to comprise a first gene for precursor IL-1β (preIL-β) operably linked to a promoter, and a second gene selected from the group consisting of: (a) a gene for Interleukin-1β Converting Enzyme (ICE), (b) a gene for an ICE-like molecule capable of processing preIL-β to mature IL-β (matIL-β) and (c) a gene for a test composition to be evaluated, the second gene being operably linked to a promoter;

the first and second genes being stably incorporated into the cell;

culturing the cell a a temperature of 31° C. to 33° C., under conditions and for a period of time sufficient for expression of the first and second genes by the cell;

applying to the cell a test composition to be evaluated when the second gene is a gene for ICE or an ICE-like molecule capable of processing preIL-β to matIL-β; and monitoring the cell or the cell environment for a change in the concentration of preIL-1β or matIL-1β, as compared To the concentration of preILβ or matIL-1β in the absence of the test composition, which change identifies the test composition as a composition having activity in IL-1β processing and secretory pathways.

8. The method of claim 7, wherein the cell is cultured at a temperature of 31° C.

9. The method of claim 7, wherein the cell is cultured at a temperature of 32° C.

10. The method of claim 7, wherein the cell is cultured at a temperature of 33° C.

11. The method of any one of claims 4 or 7, wherein the cell is cultured for at least 24 hours.

12. The method of any one of claims 4 or 7, wherein the cell is culted for at least 48 hours.

13. The method of any one of claims 4 or 7, wherein the cell is cultured for at least 72 hours.

14. The method of any one of claims 1 or 4, wherein the cell is cultured at a temperature of 31° C. to 33° C.

15. The method of any one of claims 1, 4, or 7, wherein said cell is a Chinese hamster ovary cell, CV-1 cell, mouse NIH-3T3 cell or a monkey kidney epithelial cell.

16. The method of any one of claims 1, 4, or 7, wherein said cell is a monkey kidney epithelial cell.

17. The method of any one of claims 1, 4, or 7, wherein said cell is a COS-1 cell.

18. The method of any one of claims 1, 4, or 7, wherein said test composition promotes the secretion of matIL-1β.

19. The method of any one of claims 1, 4, or 7, wherein said test composition promotes the secretion of preIL-1β.

20. The method of any one of claims 1, 4, or 7, wherein said test composition has ICE-like activity.

21. The method of any one of claims 1, 4, or 7, wherein said test composition binds so the prodomain of preIL-1β.

22. The method of any one of claims 1, 4, or 7, wherein said test composition binds to ICE, at a site other than the ICE active site, to inhibit the processing of preIL-1β or release of preIL-1β or matIL-1β.

23. The method of any one of claims 1, 4, or 7, wherein said test composition modifies preIL-1β or ICE such that preIL-1β or ICE are not processed to an active form.

24. The method of any one of claims 1, 4, or 7, wherein the second gene is for ICE.

25. The method of any one of claims 1, 4, or 7, wherein the second gene is for an ICE-like molecule.

26. A method for identifying a modulator of Interleukin-1 β Converting Enzyme (ICE) or an ICE-like molecule, comprising:

providing a non-naturally occurring cell that has been modified to comprise a first gene for ICE or an ICE-like molecule and a second gene for a substrate of ICE or the ICE-like molecule, the substrate being processed from a precursor form to a mature form by ICE or the ICE-like molecule;

the first and second genes being stably incorporated into the cell;

culturing the cell at a temperature of 31° C. to the 33° C., under conditions and for a period of time sufficient for expression of the first and second genes by the cell;

applying to the cell a test composition to be evaluated; and monitoring the cell or the cell environment for a change in the concentration of the precursor form or mature form of the substrate, as compared to the concentration of the precursor form or mature form of the substrate in the absence of the test composition, which change identifies the test composition as a modulator of ICE or the ICE-like molecule.

27. The method of claim 26, wherein the cell is a Chinese hamster ovary cell, CV-1 cell, mouse NIH-3T3 cell or a monkey kidney epithelial cell.

28. The method of claim 26, wherein the cell is a monkey kidney epithelial cell.

29. The method of claim 26, wherein the cell is a COS-1 cell.

30. A method for identifying a modulator of Interleukin-1β Converting Enzyme (ICE) or an ICE-like molecule, comprising:

providing a non-naturally occurring cell that has been modified to comprise a first gene for ICE or an ICE-like molecule, wherein the cell naturally expresses a second gene for a substrate of ICE or the ICE-like molecule, the substrate being processed from a precursor form to a mature form by ICE or the ICE-like molecule;

the first and second genes being stably incorporated into the cell;

culturing the cell at a temperature of 31° C. to 33° C., under conditions and for a period of time sufficient for expression of the first and second genes by the cell;

applying to the cell a test composition to be evaluated; and monitoring the cell or the cell environment for a change in the concentration of the precursor form or mature form of the substrate, as compared to the concentration of the precursor form or mature form of the substrate in the absence of to test composition, which change identifies the test composition as a modulator of ICE or the ICE-like molecule.

31. A method for identifying a modulator of Interleukin-1β Converting Enzyme (ICE) or an ICE-like molecule, comprising:

providing a non-naturally occurring cell that has been modified to comprise a first gene for ICE or an ICE-like molecule, wherein the cell naturally expresses a second gene for precursor IL-1β (preIL-1β);

the first and second genes being stably incorporated into the cell;

culturing the cell at a temperature of 31° C. to 33° C., under conditions and for a period of time sufficient for expression of the first and second genes by the cell;

applying to the cell a test composition to be evaluated; and monitoring the cell or the cell environment for a change in the concentration of preIL-1β or matIL-1β, as compared to be concentration of preIL-1 β or matIL-1β in the absence of the test composition, which change identifies the test composition as a modulator of ICE or the ICE-like molecule.

32. The method of anyone of claims 26, 30, or 31, wherein the cell is cultured at a temperature of 31° C.

33. The method of anyone of claims 26, 30, or 31, wherein the cell is cultured at a temperature of 32° C.

34. The method of anyone of claims 26, 30, or 31, wherein the cell is cultured at a temperature of 33° C.

35. The method of any one of claims 26, 30, or 31, wherein the cell is cultured for at least 24 hours.

36. The method of any one of claims 26, 30, or 31, wherein the cell is cultured for at least 48 hours.

37. The method of any one of claims 26, 30, or 31, wherein the cell is cultured for at least 72 hours.

38. The method of any one of claims 26, 30, or 31, wherein the first gene is for ICE.

39. The method of any one of claims 26, 30, or 31, wherein the first gene is for an ICE-like molecule.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 1215 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: HOMO SAPIENS (ix) FEATURE:
      (A) NAME/KEY: CDS
      (B) LOCATION: 1..1215

(xi) SEQUENCE DESCRIPTION: SEQ ID NO:1:

```
ATG GCC GAC AAG GTC CTG AAG GAG AAG AGA AAG CTG TTT ATC CGT TCC      48
Met Ala Asp Lys Val Leu Lys Glu Lys Arg Lys Leu Phe Ile Arg Ser
 1               5                  10                  15

ATG GGT GAA GGT ACA ATA AAT GGC TTA CTG GAT GAA TTA TTA CAG ACA      96
Met Gly Glu Gly Thr Ile Asn Gly Leu Leu Asp Glu Leu Leu Gln Thr
```

|  |  |  |  |  | 20 |  |  |  | 25 |  |  |  | 30 |  |  |  |
|---|---|---|---|---|---|---|---|---|---|---|---|---|---|---|---|---|
| AGG | GTG | CTG | AAC | AAG | GAA | GAG | ATG | GAG | AAA | GTA | AAA | CGT | GAA | AAT | GCT | 144 |
| Arg | Val | Leu | Asn | Lys | Glu | Glu | Met | Glu | Lys | Val | Lys | Arg | Glu | Asn | Ala |  |
|  |  |  |  | 35 |  |  |  |  | 40 |  |  |  |  | 45 |  |  |
| ACA | GTT | ATG | GAT | AAG | ACC | CGA | GCT | TTG | ATT | GAC | TCC | GTT | ATT | CCG | AAA | 192 |
| Thr | Val | Met | Asp | Lys | Thr | Arg | Ala | Leu | Ile | Asp | Ser | Val | Ile | Pro | Lys |  |
|  | 50 |  |  |  |  | 55 |  |  |  |  | 60 |  |  |  |  |  |
| GGG | GCA | CAG | GCA | TGC | CAA | ATT | TGC | ATC | ACA | TAC | ATT | TGT | GAA | GAA | GAC | 240 |
| Gly | Ala | Gln | Ala | Cys | Gln | Ile | Cys | Ile | Thr | Tyr | Ile | Cys | Glu | Glu | Asp |  |
| 65 |  |  |  |  | 70 |  |  |  |  | 75 |  |  |  |  | 80 |  |
| AGT | TAC | CTG | GCA | GGG | ACG | CTG | GGA | CTC | TCA | GCA | GAT | CAA | ACA | TCT | GGA | 288 |
| Ser | Tyr | Leu | Ala | Gly | Thr | Leu | Gly | Leu | Ser | Ala | Asp | Gln | Thr | Ser | Gly |  |
|  |  |  |  | 85 |  |  |  |  | 90 |  |  |  |  | 95 |  |  |
| AAT | TAC | CTT | AAT | ATG | CAA | GAC | TCT | CAA | GGA | GTA | CTT | TCT | TCC | TTT | CCA | 336 |
| Asn | Tyr | Leu | Asn | Met | Gln | Asp | Ser | Gln | Gly | Val | Leu | Ser | Ser | Phe | Pro |  |
|  |  |  |  | 100 |  |  |  |  | 105 |  |  |  |  | 110 |  |  |
| GCT | CCA | CAG | GCA | GTG | CAG | GAC | AAC | CCA | GCT | ATG | CCC | ACA | TCC | TCA | GGC | 384 |
| Ala | Pro | Gln | Ala | Val | Gln | Asp | Asn | Pro | Ala | Met | Pro | Thr | Ser | Ser | Gly |  |
|  |  | 115 |  |  |  |  | 120 |  |  |  |  | 125 |  |  |  |  |
| TCA | GAA | GGG | AAT | GTC | AAG | CTT | TGC | TCC | CTA | GAA | GAA | GCT | CAA | AGG | ATA | 432 |
| Ser | Glu | Gly | Asn | Val | Lys | Leu | Cys | Ser | Leu | Glu | Glu | Ala | Gln | Arg | Ile |  |
|  |  | 130 |  |  |  |  | 135 |  |  |  |  | 140 |  |  |  |  |
| TGG | AAA | CAA | AAG | TCG | GCA | GAG | ATT | TAT | CCA | ATA | ATG | GAC | AAG | TCA | AGC | 480 |
| Trp | Lys | Gln | Lys | Ser | Ala | Glu | Ile | Tyr | Pro | Ile | Met | Asp | Lys | Ser | Ser |  |
| 145 |  |  |  |  | 150 |  |  |  |  | 155 |  |  |  |  | 160 |  |
| CGC | ACA | CGT | CTT | GCT | CTC | ATT | ATC | TGC | AAT | GAA | GAA | TTT | GAC | AGT | ATT | 528 |
| Arg | Thr | Arg | Leu | Ala | Leu | Ile | Ile | Cys | Asn | Glu | Glu | Phe | Asp | Ser | Ile |  |
|  |  |  |  | 165 |  |  |  |  | 170 |  |  |  |  | 175 |  |  |
| CCT | AGA | AGA | ACT | GGA | GCT | GAG | GTT | GAC | ATC | ACA | GGC | ATG | ACA | ATG | CTG | 576 |
| Pro | Arg | Arg | Thr | Gly | Ala | Glu | Val | Asp | Ile | Thr | Gly | Met | Thr | Met | Leu |  |
|  |  |  | 180 |  |  |  |  | 185 |  |  |  |  | 190 |  |  |  |
| CTA | CAA | AAT | CTG | GGG | TAC | AGC | GTA | GAT | GTG | AAA | AAA | AAT | CTC | ACT | GCT | 624 |
| Leu | Gln | Asn | Leu | Gly | Tyr | Ser | Val | Asp | Val | Lys | Lys | Asn | Leu | Thr | Ala |  |
|  |  |  | 195 |  |  |  |  | 200 |  |  |  |  | 205 |  |  |  |
| TCG | GAC | ATG | ACT | ACA | GAG | CTG | GAG | GCA | TTT | GCA | CAC | CGC | CCA | GAG | CAC | 672 |
| Ser | Asp | Met | Thr | Thr | Glu | Leu | Glu | Ala | Phe | Ala | His | Arg | Pro | Glu | His |  |
| 210 |  |  |  |  | 215 |  |  |  |  | 220 |  |  |  |  |  |  |
| AAG | ACC | TCT | GAC | AGC | ACG | TTC | CTG | GTG | TTC | ATG | TCT | CAT | GGT | ATT | CGG | 720 |
| Lys | Thr | Ser | Asp | Ser | Thr | Phe | Leu | Val | Phe | Met | Ser | His | Gly | Ile | Arg |  |
| 225 |  |  |  |  | 230 |  |  |  |  | 235 |  |  |  |  | 240 |  |
| GAA | GGC | ATT | TGT | GGG | AAG | AAA | CAC | TCT | GAG | CAA | GTC | CCA | GAT | ATA | CTA | 768 |
| Glu | Gly | Ile | Cys | Gly | Lys | Lys | His | Ser | Glu | Gln | Val | Pro | Asp | Ile | Leu |  |
|  |  |  | 245 |  |  |  |  | 250 |  |  |  |  | 255 |  |  |  |
| CAA | CTC | AAT | GCA | ATC | TTT | AAC | ATG | TTG | AAT | ACC | AAG | AAC | TGC | CCA | AGT | 816 |
| Gln | Leu | Asn | Ala | Ile | Phe | Asn | Met | Leu | Asn | Thr | Lys | Asn | Cys | Pro | Ser |  |
|  |  | 260 |  |  |  |  | 265 |  |  |  |  | 270 |  |  |  |  |
| TTG | AAG | GAC | AAA | CCG | AAG | GTG | ATC | ATC | ATC | CAG | GCC | TGC | CGT | GGT | GAC | 864 |
| Leu | Lys | Asp | Lys | Pro | Lys | Val | Ile | Ile | Ile | Gln | Ala | Cys | Arg | Gly | Asp |  |
|  |  | 275 |  |  |  |  | 280 |  |  |  |  | 285 |  |  |  |  |
| AGC | CCT | GGT | GTG | GTG | TGG | TTT | AAA | GAT | TCA | GTA | GGA | GTT | TCT | GGA | AAC | 912 |
| Ser | Pro | Gly | Val | Val | Trp | Phe | Lys | Asp | Ser | Val | Gly | Val | Ser | Gly | Asn |  |
|  | 290 |  |  |  |  | 295 |  |  |  |  | 300 |  |  |  |  |  |
| CTA | TCT | TTA | CCA | ACT | ACA | GAA | GAG | TTT | GAG | GAT | GAT | GCT | ATT | AAG | AAA | 960 |
| Leu | Ser | Leu | Pro | Thr | Thr | Glu | Glu | Phe | Glu | Asp | Asp | Ala | Ile | Lys | Lys |  |
| 305 |  |  |  |  | 310 |  |  |  |  | 315 |  |  |  |  | 320 |  |
| GCC | CAC | ATA | GAG | AAG | GAT | TTT | ATC | GCT | TTC | TGC | TCT | TCC | ACA | CCA | GAT | 1008 |
| Ala | His | Ile | Glu | Lys | Asp | Phe | Ile | Ala | Phe | Cys | Ser | Ser | Thr | Pro | Asp |  |
|  |  |  |  | 325 |  |  |  |  | 330 |  |  |  |  | 335 |  |  |
| AAT | GTT | TCT | TGG | AGA | CAT | CCC | ACA | ATG | GGC | TCT | GTT | TTT | ATT | GGA | AGA | 1056 |

```
Asn Val Ser Trp Arg His Pro Thr Met Gly Ser Val Phe Ile Gly Arg
            340                 345                 350

CTC ATT GAA CAT ATG CAA GAA TAT GCC TGT TCC TGT GAT GTG GAG GAA    1104
Leu Ile Glu His Met Gln Glu Tyr Ala Cys Ser Cys Asp Val Glu Glu
        355                 360                 365

ATT TTC CGC AAG GTT CGA TTT TCA TTT GAG CAG CCA GAT GGT AGA GCG    1152
Ile Phe Arg Lys Val Arg Phe Ser Phe Glu Gln Pro Asp Gly Arg Ala
    370                 375                 380

CAG ATG CCC ACC ACT GAA AGA GTG ACT TTG ACA AGA TGT TTC TAC CTC    1200
Gln Met Pro Thr Thr Glu Arg Val Thr Leu Thr Arg Cys Phe Tyr Leu
385                 390                 395                 400

TTC CCA GGA CAT TAA                                                 1215
Phe Pro Gly His
            405
```

(2) INFORMATION FOR SEQ ID NO:2:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Asp Lys Val Leu Lys Glu Lys Arg Lys Leu Phe Ile Arg Ser
 1               5                  10                  15

Met Gly Glu Gly Thr Ile Asn Gly Leu Leu Asp Glu Leu Leu Gln Thr
                20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
                100                 105                 110

Ala Pro Gln Ala Val Gln Asp Asn Pro Ala Met Pro Thr Ser Ser Gly
            115                 120                 125

Ser Glu Gly Asn Val Lys Leu Cys Ser Leu Glu Glu Ala Gln Arg Ile
        130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
                180                 185                 190

Leu Gln Asn Leu Gly Tyr Ser Val Asp Val Lys Lys Asn Leu Thr Ala
            195                 200                 205

Ser Asp Met Thr Thr Glu Leu Glu Ala Phe Ala His Arg Pro Glu His
        210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255
```

```
Gln Leu Asn Ala Ile Phe Asn Met Leu Asn Thr Lys Asn Cys Pro Ser
            260                 265                 270

Leu Lys Asp Lys Pro Lys Val Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His
```

(2) INFORMATION FOR SEQ ID NO:3:

(i) SEQUENCE CHARACTERISTICS:
        (A) LENGTH: 846 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HOMO SAPIENS (ix) FEATURE:
        (A) NAME/KEY: CDS
        (B) LOCATION: 19..828

(xi) SEQUENCE DESCRIPTION: SEQ ID NO:3:

```
CTCGAGTCTG AAGCAGCC ATG GCA GAA GTA CCT GAG CTC GCC AGT GAA ATG        51
                   Met Ala Glu Val Pro Glu Leu Ala Ser Glu Met
                    1               5                      10

ATG GCT TAT TAC AGT GGC AAT GAG GAT GAC TTG TTC TTT GAA GCT GAT        99
Met Ala Tyr Tyr Ser Gly Asn Glu Asp Asp Leu Phe Phe Glu Ala Asp
            15                  20                  25

GGC CCT AAA CAG ATG AAG TGC TCC TTC CAG GAC CTG GAC CTC TGC CCT       147
Gly Pro Lys Gln Met Lys Cys Ser Phe Gln Asp Leu Asp Leu Cys Pro
        30                  35                  40

CTG GAT GGC GGC ATC CAG CTA CGA ATC TCC GAC CAC CAC TAC AGC AAG       195
Leu Asp Gly Gly Ile Gln Leu Arg Ile Ser Asp His His Tyr Ser Lys
    45                  50                  55

GGC TTC AGG CAG GCC GCG TCA GTT GTT GTG GCC ATG GAC AAG CTG AGG       243
Gly Phe Arg Gln Ala Ala Ser Val Val Val Ala Met Asp Lys Leu Arg
60                  65                  70                  75

AAG ATG CTG GTT CCC TGC CCA CAG ACC TTC CAG GAG AAT GAC CTG AGC       291
Lys Met Leu Val Pro Cys Pro Gln Thr Phe Gln Glu Asn Asp Leu Ser
                80                  85                  90

ACC TTC TTT CCC TTC ATC TTT GAA GAA GAA CCT ATC TTC TTC GAC ACA       339
Thr Phe Phe Pro Phe Ile Phe Glu Glu Glu Pro Ile Phe Phe Asp Thr
```

-continued

```
                    95                  100                 105
TGG GAT AAC GAG GCT TAT GTG CAC GAT GCA CCT GTA CGA TCA CTG AAC        387
Trp Asp Asn Glu Ala Tyr Val His Asp Ala Pro Val Arg Ser Leu Asn
            110                 115                 120

TGC ACG CTC CGG GAC TCA CAG CAA AAA AGC TTG GTG ATG TCT GGT CCA        435
Cys Thr Leu Arg Asp Ser Gln Gln Lys Ser Leu Val Met Ser Gly Pro
    125                 130                 135

TAT GAA CTG AAA GCT CTC CAC CTC CAG GGA CAG GAT ATG GAG CAA CAA        483
Tyr Glu Leu Lys Ala Leu His Leu Gln Gly Gln Asp Met Glu Gln Gln
140                 145                 150                 155

GTG GTG TTC TCC ATG TCC TTT GTA CAA GGA GAA GAA AGT AAT GAC AAA        531
Val Val Phe Ser Met Ser Phe Val Gln Gly Glu Glu Ser Asn Asp Lys
                160                 165                 170

ATA CCT GTG GCC TTG GGC CTC AAG GAA AAG AAT CTG TAC CTG TCC TGC        579
Ile Pro Val Ala Leu Gly Leu Lys Glu Lys Asn Leu Tyr Leu Ser Cys
            175                 180                 185

GTG TTG AAA GAT GAT AAG CCC ACT CTA CAG CTG GAG AGT GTA GAT CCC        627
Val Leu Lys Asp Asp Lys Pro Thr Leu Gln Leu Glu Ser Val Asp Pro
    190                 195                 200

AAA AAT TAC CCA AAG AAG AAG ATG GAA AAG CGA TTT GTC TTC AAC AAG        675
Lys Asn Tyr Pro Lys Lys Lys Met Glu Lys Arg Phe Val Phe Asn Lys
205                 210                 215

ATA GAA ATC AAT AAC AAG CTG GAA TTT GAG TCT GCC CAG TTC CCC AAC        723
Ile Glu Ile Asn Asn Lys Leu Glu Phe Glu Ser Ala Gln Phe Pro Asn
220             225                 230                 235

TGG TAC ATC AGC ACC TCT CAA GCA GAA AAC ATG CCC GTC TTC CTG GGA        771
Trp Tyr Ile Ser Thr Ser Gln Ala Glu Asn Met Pro Val Phe Leu Gly
            240                 245                 250

GGG ACC AAA GGC GGC CAG GAT ATA ACT GAC TTC ACC ATG CAA TTT GTG        819
Gly Thr Lys Gly Gly Gln Asp Ile Thr Asp Phe Thr Met Gln Phe Val
    255                 260                 265

TCT TCC TAAAGAGAGC TGTACGGATC C                                        846
Ser Ser
        270
```

(2) INFORMATION FOR SEQ ID NO:4:

(i) SEQUENCE CHARACTERISTICS:
　　　　(A) LENGTH: 269 amino acids
　　　　(B) TYPE: amino acid
　　　　(D) TOPOLOGY: linear (ii) MOLECULE TYPE: protein (xi) SEQUENCE DESCRIPTION: SEQ ID NO:4:

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110
```

```
Tyr Val His Asp Ala Pro Val Arg Ser Leu Asn Cys Thr Leu Arg Asp
        115                 120                 125
Ser Gln Gln Lys Ser Leu Val Met Ser Gly Pro Tyr Glu Leu Lys Ala
    130                 135                 140
Leu His Leu Gln Gly Gln Asp Met Glu Gln Gln Val Val Phe Ser Met
145                 150                 155                 160
Ser Phe Val Gln Gly Glu Glu Ser Asn Asp Lys Ile Pro Val Ala Leu
                165                 170                 175
Gly Leu Lys Glu Lys Asn Leu Tyr Leu Ser Cys Val Leu Lys Asp Asp
                180                 185                 190
Lys Pro Thr Leu Gln Leu Glu Ser Val Asp Pro Lys Asn Tyr Pro Lys
            195                 200                 205
Lys Lys Met Glu Lys Arg Phe Val Phe Asn Lys Ile Glu Ile Asn Asn
        210                 215                 220
Lys Leu Glu Phe Glu Ser Ala Gln Phe Pro Asn Trp Tyr Ile Ser Thr
225                 230                 235                 240
Ser Gln Ala Glu Asn Met Pro Val Phe Leu Gly Gly Thr Lys Gly Gly
                245                 250                 255
Gln Asp Ile Thr Asp Phe Thr Met Gln Phe Val Ser Ser
                260                 265
```

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (xi) SEQUENCE DESCRIPTION: SEQ ID NO:5:

```
CCCCTCGAGT CTGAAGCAGC CATGGCAGAA GTACCT                              36
```

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (xi) SEQUENCE DESCRIPTION: SEQ ID NO:6:

```
CCCGGATCCG TACAGCTCTC TTTAGGAAGA CACAAA                              36
```

(2) INFORMATION FOR SEQ ID NO:7:

(i) SEQUENCE CHARACTERISTICS:
        (A) LENGTH: 36 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: HOMO SAPIENS (xi) SEQUENCE DESCRIPTION: SEQ ID NO:7:

CCCATGCATG GAAGACACAA ATTGCATGGT GAAGTC                                      36

(2) INFORMATION FOR SEQ ID NO:8:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: HOMO SAPIENS (xi) SEQUENCE DESCRIPTION: SEQ ID NO:8:

CCCCTCGAGG CCATGGCCGA CAAGGTCCTG AAGGAG                                      36

(2) INFORMATION FOR SEQ ID NO:9:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: HOMO SAPIENS (xi) SEQUENCE DESCRIPTION: SEQ ID NO:9:

CCCCTCGAGA TGAACCCAGC TATGCCCACA TCCTCA                                      36

(2) INFORMATION FOR SEQ ID NO:10:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: HOMO SAPIENS (xi) SEQUENCE DESCRIPTION: SEQ ID NO:10:

CCCGGATCCT TAATCTTTAA ACCACACCAC ACCAGG					36

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (xi) SEQUENCE DESCRIPTION: SEQ ID NO:11:

CCCCTCGAGA TGGCTATTAA GAAAGCCCAC ATAGAG					36

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS (xi) SEQUENCE DESCRIPTION: SEQ ID NO:12:

CCCGGATCCA TTTTAATGTC CTGGGAAGAG GTAGAA					36

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: SYNTHETIC PRIMER (xi) SEQUENCE DESCRIPTION: SEQ ID NO:13:

GATAACCAGG CTTATGTGCA CAACGTCCCT GTACGATCAC TGAACTGC					48

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: SYNTHETIC PRIMER (xi) SEQUENCE DESCRIPTION: SEQ ID NO:14:

GCAGTTCAGT GATCGTACAG GGACGTTGTG CACATAAGCC ACGTTATC                    48

(2) INFORMATION FOR SEQ ID NO:15:

(i) SEQUENCE CHARACTERISTICS:
             (A) LENGTH: 40 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: SYNTHETIC PRIMER (xi) SEQUENCE DESCRIPTION: SEQ ID NO:15:

CGAAGGTGAT CATCATCCAG GCCTCCCGTG GTGACAGCCC                             40

(2) INFORMATION FOR SEQ ID NO:16:

(i) SEQUENCE CHARACTERISTICS:
             (A) LENGTH: 40 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: SYNTHETIC PRIMER (xi) SEQUENCE DESCRIPTION: SEQ ID NO:16:

GAGGCCTGGA TGATGATCAC CTTCGGTTTG TCCTTCAAAC                             40

(2) INFORMATION FOR SEQ ID NO:17:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: SYNTHETIC PRIMER (xi) SEQUENCE DESCRIPTION: SEQ ID NO:17:

CATCATCCAG GCCGCCCGTG GTGACAGCCC                                        30

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: SYNTHETIC PRIMER (xi) SEQUENCE DESCRIPTION: SEQ ID NO:18:

GCCCTGGTGT GGTGTGGTTT AAAGCTTCAG TAGGAGTTTC    40

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: SYNTHETIC PRIMER (xi) SEQUENCE DESCRIPTION: SEQ ID NO:19:

GCTTTAAACC ACACCACACC AGGGCTGTCA CCACGGCAGG    40